US010689462B2

United States Patent
Thompson et al.

(10) Patent No.: US 10,689,462 B2
(45) Date of Patent: *Jun. 23, 2020

(54) THERAPEUTIC AND IMAGING COMPOSITIONS AND USES THEREOF

(71) Applicant: Purdue Research Foundation, West Lafayette, IN (US)

(72) Inventors: David H. Thompson, West Lafayette, IN (US); Aditya Kulkarni, West Lafayette, IN (US); Christopher Collins, West Lafayette, IN (US); Yawo Mondjinou, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/978,872

(22) Filed: May 14, 2018

(65) Prior Publication Data

US 2018/0258192 A1  Sep. 13, 2018

Related U.S. Application Data

(63) Continuation of application No. 14/889,722, filed as application No. PCT/US2014/037134 on May 7, 2014, now Pat. No. 10,000,581.

(60) Provisional application No. 61/820,658, filed on May 7, 2013, provisional application No. 61/820,597, filed on May 7, 2013.

(51) Int. Cl.
| | |
|---|---|
| *A61K 8/00* | (2006.01) |
| *C08B 37/16* | (2006.01) |
| *G01N 33/68* | (2006.01) |
| *A61K 47/60* | (2017.01) |
| *A61K 31/724* | (2006.01) |
| *A61K 31/765* | (2006.01) |
| *A61K 51/06* | (2006.01) |
| *A61K 51/12* | (2006.01) |
| *A61K 47/61* | (2017.01) |
| *A61K 47/69* | (2017.01) |
| *C08G 83/00* | (2006.01) |
| *A61K 47/54* | (2017.01) |

(52) U.S. Cl.
CPC ........ *C08B 37/0015* (2013.01); *A61K 31/724* (2013.01); *A61K 31/765* (2013.01); *A61K 47/60* (2017.08); *A61K 47/61* (2017.08); *A61K 47/6951* (2017.08); *A61K 51/065* (2013.01); *A61K 51/1268* (2013.01); *G01N 33/6893* (2013.01); *A61K 47/547* (2017.08); *C08G 83/007* (2013.01)

(58) Field of Classification Search
None
See application file for complete search history.

(56) References Cited

U.S. PATENT DOCUMENTS

| | | | |
|---|---|---|---|
| 6,068,831 | A | 5/2000 | Platzek et al. |
| 10,000,581 | B2 | 6/2018 | Thompson et al. |
| 2013/0224881 | A1 | 8/2013 | Thompson et al. |
| 2016/0083485 | A1 | 3/2016 | Thompson et al. |

FOREIGN PATENT DOCUMENTS

| | | |
|---|---|---|
| EP | 3037097 A1 | 6/2016 |
| WO | WO-9801163 A2 | 1/1998 |
| WO | WO-2012124218 A1 | 9/2012 |
| WO | WO-2014182804 A1 | 11/2014 |

OTHER PUBLICATIONS

Li et al. "Cationic Supramolecules Composed of MultipleOligoethylenimine-Grafted b-Cyclodextrins Threaded on a Polymer Chain for Efficient Gene Delivery", Adv. Mater. 2006, 18, 2969-2974 (Year: 2006).*
Loethen et al. "Synthesis, Characterization, and pH-Triggered Dethreading of α-Cyclodextrin-Poly(ethylene glycol) Polyrotaxanes Bearing Cleavable Endcaps.", Biomacromolecules, vol. 7, No. 9, 2006 (Year: 2006).*
"U.S. Appl. No. 14/889,722, Non Final Office Action dated Aug. 7, 2017", 13 pgs.
"U.S. Appl. No. 14/889,722, Notice of Allowability dated Apr. 12, 2018", 4 pgs.
"U.S. Appl. No. 14/889,722, Notice of Allowance dated Feb. 14, 2018", 7 pgs.
"U.S. Appl. No. 14/889,722, Preliminary Amendment filed Nov. 6, 2015", 10 pgs.
"U.S. Appl. No. 14/889,722, Response filed May 9, 2017 to Restriction Requirement dated Mar. 9, 2017", 10 pgs.
"U.S. Appl. No. 14/889,722, Response filed Dec. 7, 2017 to Non Final Office Action dated Aug. 7, 2017", 8 pgs.
"U.S. Appl. No. 14/889,722, Restriction Requirement dated Mar. 9, 2017", 9 pgs.
"U.S. Appl. No. 14/889,722, Supplemental Response filed Jun. 28, 2017 to Restriction Requirement dated Mar. 9, 2017", 10 pgs.
"European Application Serial No. 14794124.9, Communication Pursuant to Article 94(3) EPC dated Feb. 9, 2018", 8 pgs.
"European Application Serial No. 14794124.9, Extended European Search Report dated Jan. 31, 2017", 19 pgs.
"European Application Serial No. 14794124.9, Response Filed Aug. 25, 2017 to Extended European Search Report dated Jan. 31, 2017", 11 pgs.
"European Patent Application Ser. No. 14794124.9, Office Action dated Jan. 15, 2016", 2 pgs.

(Continued)

*Primary Examiner* — James W Rogers
(74) *Attorney, Agent, or Firm* — Schwegman Lundberg & Woessner, P.A.

(57) ABSTRACT

Various embodiments of the present invention are directed to polyrotaxanes comprising a poloxamer core and at least one cyclodextrin and methods for treating Niemann-Pick type C (NPC) and imaging (e.g., MRI) using the polyrotaxanes various embodiments of the present invention.

8 Claims, No Drawings

(56) References Cited

OTHER PUBLICATIONS

"European Patent Application Ser. No. 14794124.9, Response filed Jul. 13, 2016 to Office Action dated Jan. 15, 2016", 8 pgs.

"International Application Serial No. PCT/US2014/037134, International Preliminary Report on Patentability dated Nov. 19, 2015", 6 pgs.

"International Application Serial No. PCT/US2014/037134, International Search Report dated Aug. 29, 2014", 3 pgs.

"International Application Serial No. PCT/US2014/037134, Written Opinion dated Aug. 29, 2014", 4 pgs.

Battistini, et al., "High-Relaxivity Magnetic Resonance Imaging (MRI) Contrast Agent Based on Supramolecular Assembly between a Gadolinium Chelate, a Modified Dextran, and Poly-β-Cyclodextrin", Che. Eur. J. vol. 14, (2008), 4551-4561.

Bryson, Joshua M, et al., "A beta-cyclodextrin Click Cluster decorated with seven paramagnetic chelates containing two water exchange sites", Bioconjugate Chemistry, Acs, Washington, DC, US, vol. 19, No. 8, (Aug. 1, 2008), 1505-1509.

Chuan, Yang, et al., "Thermoresponsive Behavior of Cationic Polyrotaxane Composed of Multiple Pentaethylenehexamine-grafted [alpha]-Cyclodextrins Threaded on Polypropylene oxide)-Poly(ethylene oxide)-Poly(propylene oxide) Triblock Copolymer", Journal of Physical Chemistry Part B: Condensed Matter, Materials, Surfaces, Interfaces & Biophysical, vol. 113, (Jan. 22, 2009), 682-690.

Collins, et al., "Synthesis, Characterization, and Evaluation of Pluronic-Based β-Cyclodextrin Polyrotaxanes for Mobilization of Accumulated Cholesterol from Niemann-Pick Type C Fibroblasts", Biochemistry, vol. 52, (Apr. 5, 2013), 3242-3253.

Cristin, Davidson D, et al., "Chronic Cyclodextrin Treatment of Murine Niemann-Pick C Disease Ameliorates Neuronal Cholesterol and Glycosphingolipid Storage and Disease Progression", PLOS ONE, vol. 4, No. 9, (Sep. 11, 2009), 6951 pgs (15 pgs total).

Lee, et al., "Synthesis of main chain type polyrotaxanes by new click polymerization", Macromolecules, vol. 43, No. 9, (Jan. 1, 2010), 4070-4080.

Lee, Young-Gi, et al., "Synthesis of Main-Chain-Type Polyrotaxanes by New Click Polymerization Using Homoditopic Nitrile N-Oxides via Rotaxanation—Polymerization Protocol", Macromolecules, vol. 43, No. 9, (Feb. 4, 2010), 4070-4080.

Loethen, et al., "Biomedical Applications of Cyclodextrin Based Polyrotaxanes", Polymer Reviews, vol. 47, No. 3, (2007), 383-418.

Nakazono, Kazuko, et al., "High-Yield One-Pot Synthesis of Permethylated R-Cyclodextrin-based Polyrotaxane in Hydrocarbon Solvent through an Efficient Heterogeneous Reaction", Macromolecules, 43, (2010), 691-696.

Rosenbaum, A, et al., "Endocytosis of beta-cyclodextrins is responsible for cholesterol reduction in Niemann-Pick type C mutant cells", Proceedings of the National Academy of Sciences, vol. 107, No. 12, (Mar. 23, 2010), 5477-5482.

Shuo, Li, et al., "Polyrotaxane-based triblock copolymers synthesized via ATRP of isopropylacrylamide initiated from the terminals of polypseudorotaxane of Br end-capped pluronic 17R4 and i-cyclodextrins", Science China Chemistry, Sp Science China Press, Heidelberg, vol. 55, No. 6, (May 8, 2012), 1115-1124.

Song, Y, et al., "Synthesis of multimeric MR contrast agents for cellular imaging", Journal of the American Chemical Society, American Chemical Society, US, vol. 130, No. 21, (May 28, 2008), 6662-6663.

Tooru, Ooya, et al., "Carboxyethylester-polyrotaxanes as a new calcium chelating polymer: synthesis, calcium binding and mechanism of trypsin inhibition", International Journal of Pharmaceutics, vol. 242, No. 1-2, (Aug. 1, 2002), 47-54.

Tooru, Ooya, et al., "Preparation of [alpha]-Cyclodextrin-Terminated Polyrotaxane Consisting of [beta]-Cyclodextrins and Pluronic as a Building Block of a Biodegradable Network", Macromolecular Bioscience, vol. 5, No. 5, (May 23, 2005), 379-383.

Yang, C, et al., "Synthesis of polyrotaxanes consisting of multiple alpha-cyclodextrin rings threaded on reverse Pluronic PPO-PEO-PPO triblock copolymers based on block-selected inclusion complexation", European Polymer Journal, Pergamon Press Ltd. Oxford, GB, vol. 45, No. 5, (May 1, 2009), 1570-1579.

Yawo, M, et al., "Synthesis of 2-Hydroxypropyl-[beta]-cyclodextrin/Pluronic-Based Polyrotaxanes via Heterogeneous Reaction as Potential Niemann-Pick Type C Therapeutics", Biomacromolecules, vol. 14, No. 12, (Dec. 9, 2013), 4189-4197.

"European Application Serial No. 14794124.9, Response filed Aug. 15, 2018 to Communication Pursuant to Article 94(3) EPC dated Feb. 9, 2018", 8 pgs.

"European Application Serial No. 14794124.9, Communication Pursuant to Article 94(3) EPC dated Nov. 7, 2019", 6 pgs.

"Handbook of Pharmaceutical Excipients", Poloxamer, Sixth Edition, Pharmaceutical Press, XP055629883, (Jan. 1, 2009), 11 pgs.

* cited by examiner

THERAPEUTIC AND IMAGING COMPOSITIONS AND USES THEREOF

CROSS-REFERENCE TO RELATED APPLICATIONS

This application is a continuation of U.S. application. Ser. No. 14/889,722, filed Nov. 6, 2015, which is a U.S. National Stage Filing under 35 U.S.C. § 371 from International Application No. PCT/US2014/037134, filed on May 7, 2014 and published as WO 2014/182804 on Nov. 13, 2014, which claims the benefit of U.S. Provisional Appl. Ser. No. 61/820,658, filed May 7, 2013; and 61/820,597, filed May 7, 2013, which applications and publication are incorporated herein by reference in their entirety.

STATEMENT OF GOVERNMENT SUPPORT

This invention was made with government support under grant GM087016 awarded by the National Institutes of Health. The government has certain rights in the invention.

BACKGROUND OF THE INVENTION

Therapeutic agents and imaging contrast agents sometimes suffer drawbacks stemming from high clearance and/or high toxicity. For example, even though some studies have shown that β-cyclodextrin (α-CD) and its derivatives, including hydroxypropyl-β-cyclodextrin (HP-β-CD), may be useful in the treatment of the typically fatal disease Niemann-Pick type C (NPC), high dosages of the administered β-CDs or derivatives thereof are required since their persistence in the bloodstream is brief (>90% is cleared within 24 hours). With regard to imaging contrast agents, a majority of clinically used contrast agents, though they may have high paramagnetism, excellent relaxation enhancement, and stability, they suffer from rapid clearance from the body, such that they are ineffective, e.g., for angiographic enhancement. In some instances, nanoparticulate platforms used as carriers of, e.g., $Gd^{3+}$, though they have better pharmacokinetics than other clinically used contrast agents, suffer from issues such as acute toxicity and poor water accessibility. There is therefore a need in the art for therapeutic agents for treating, e.g., NPC, and imaging contrast agents that do not suffer from the drawbacks enumerated herein.

DETAILED DESCRIPTION OF THE INVENTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

The therapeutic agents and imaging contrast agents of the various embodiments of the present invention are based on a class of supramolecular materials known as polyrotaxanes.

A polyrotaxane is a macrocylic host molecule or molecules that is/are "threaded" onto a polymer chain of compatible dimensions via host-guest hydrophobic interactions, with the ends of the polymer chain being capped with endcapping groups. A schematic representation of a polyrotaxane is given in Scheme 1:

Scheme 1

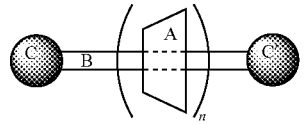

or a salt thereof (e.g., a pharmaceutically acceptable salt thereof), wherein C and C' are the same or different and represent endcapping groups; B represents the "polymer chain of compatible dimensions" to which the endcapping groups are covalently attached; A represents the macrocyclic host molecule that is "threaded" onto the polymer chain B; and n is an integer from 1 to 100 (e.g., 1 to 75, 1 to 50, 1 to 30, 5 to 15, 5 to 12, 10 to 30, 10 to 50, 1 to 20, 1 to 15, 5 to 15, 3 to 11, 1 to 12, 2 to 12 or 2 to 18), wherein n represents the number of "copies" of the macrocyclic host molecules C that are "threaded" onto the polymer chain B.

Macrocyclic Host Molecule (A)

The macrocyclic host molecule (A) can be any suitable macrocyclic host molecule, so long as the macrocylic host molecule or molecules can "thread" onto a polymer chain of compatible dimensions via host-guest hydrophobic interactions. For suitable macrocyclic host molecules, see, e.g., C. J. Collins et al., *Biochemistry* 52: 3242-3253 (2013), which is incorporated by reference as if fully set forth herein. In some embodiments, the macrocyclic host molecule (A) can be a cyclodextrin. As used herein, the term "cyclodextrin" broadly refers to macrocyclic oligosaccharides produced by the cyclization (e.g., enzymatic cyclization) of 6, 7, or 8 (+)-glucopyranoside units linked by, e.g., α-1,4-bonds to generate α-, β-, or γ-CD, respectively.

Cyclodextrins have a toroidal topology with a hydrophobic internal cavity. β-CD, and its derivatives, have garnered attention due to their use in the pharmaceutical and food industry as solubilizing agents, permeability enhancers, and active ingredient stabilizers.

In some embodiments, the macrocyclic host molecule (A) has the general formula (I):

(I)

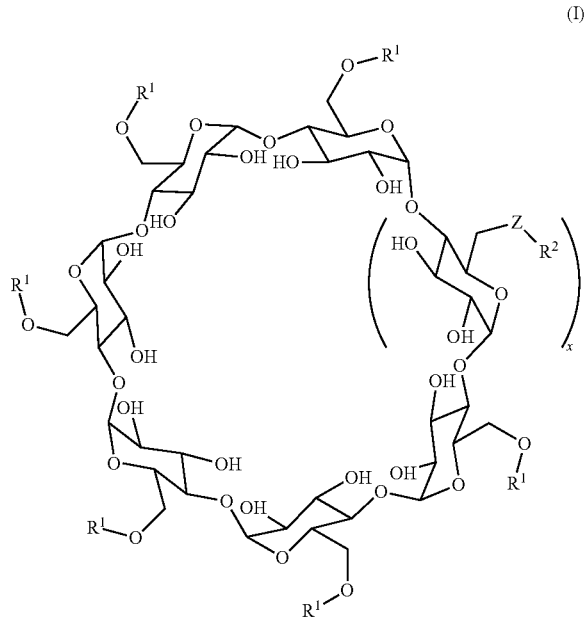

wherein each Z is independently O (oxygen) or NH; each $R^1$ and $R^2$ is independently hydrogen or a substituted or unsubstituted $(C_1-C_{20})$hydrocarbyl group (e.g., substituted or unsubstituted $(C_1-C_{12})$hydrocarbyl group; substituted or unsubstituted $(C_1-C_6)$hydrocarbyl group; or a substituted or unsubstituted $(C_1-C_3)$hydrocarbyl group), interrupted by 0 to 5 (e.g., 0-3) groups chosen from —O—, —NH—, and —S—; and x is an integer from 1 to 3. In some embodiments, each $R^1$ and $R^2$ is independently hydrogen or a $(C_1-C_{20})$hydrocarbyl group substituted with a drug radical, an imaging contrast agent radical (e.g., a radionuclide chelating moiety comprising a radionuclide or a paramagnetic nuclide chelating moiety comprising a paramagnetic nuclide) or combinations thereof.

In some embodiments, each $R^1$ is independently a substituted or unsubstituted $(C_1-C_{20})$alkyl group (e.g., substituted or unsubstituted $(C_1-C_{12})$ alkyl group; substituted or unsubstituted $(C_1-C_6)$ alkyl group; or a substituted or unsubstituted $(C_1-C_3)$ alkyl group), interrupted by 0 to 5 (e.g., 0-3) groups chosen from —O—, —NH—, and —S—; and x is an integer from 1 to 3.

In some embodiments, in the context of the compounds of the formula (I) wherein each Z is independently O or NH; each $R^1$ is independently hydrogen or a substituted or unsubstituted $(C_1-C_{20})$hydrocarbyl group, interrupted by 0 to 5 groups chosen from —O—, —NH—, and —S—; x is an integer from 1 to 3; and $R^2$ is substituted or unsubstituted $(C_1-C_{20})$hydrocarbyl group, interrupted by 0 to 5 groups chosen from —O—, —NH—, and —S—, with the proviso that at least one $R^2$ is $(C_1-C_{20})$hydrocarbyl group, interrupted by 0 to 5 groups chosen from —O—, —NH—, and —S—, substituted with a group $C(S)N(R)_2$, wherein one R is hydrogen and the other is an aryl group substituted with a radionuclide chelating moiety.

In some embodiments, each $R^1$ is hydrogen or a radical having the formula:

(II)

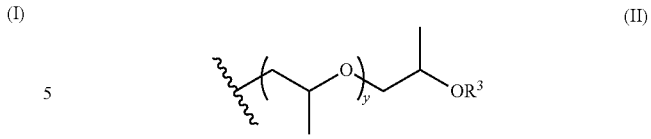

wherein y is an integer from 1 to 10 (e.g., an integer from 1 to 8, 1 to 5 or 1 to 3) and $R^3$ is hydrogen or a substituted or unsubstituted $(C_1-C_3)$hydrocarbyl group.

In other embodiments $R^1$ and $R^2$ are each, independently, hydrogen or a radical of the formula (II), wherein $R^3$ is hydrogen; Z is O; x is an integer from 1 to 3; and y is an integer from 1 to 3.

In some embodiments, the compound of the formula (I) is hydroxypropyl-β-cyclodextrin (HP-β-CD). HP-β-CD is an attractive precursor for polyrotaxane synthesis, since it is approved by the FDA as an inactive pharmaceutical ingredient and is substantially more water soluble at room temperature (0.65 g/mL in water) than β-CD. Such solubility in aqueous solution makes it a good candidate for designing well-tolerated polyrotaxanes, such as those described herein, that could enhance the pharmacokinetics and biodistribution of HP-β-CD in models of, e.g., NPC disease.

In some embodiments, each $R^1$ is independently hydrogen or a substituted or unsubstituted $(C_1-C_{20})$hydrocarbyl group, interrupted by 0 to 5 (e.g., 0-3) groups chosen from —O—, —NH—, and —S—; Z is —NH—; and $R^2$ is a $(C_1-C_{20})$hydrocarbyl group, interrupted by 0 to 5 (e.g., 0-3) groups chosen from —O—, —NH—, and —S—, substituted with a group $C(S)N(R)_2$, wherein R is hydrogen or substituted aryl (e.g., aryl substituted with a chelating moiety).

In some embodiments, each $R^1$ is independently hydrogen or a substituted or unsubstituted $(C_1-C_{20})$hydrocarbyl group, interrupted by 0 to 5 (e.g., 0-3) groups chosen from —O—, —NH—, and —S—; Z is —NH—; $R^2$ is a $(C_1-C_{20})$hydrocarbyl group, interrupted by 0 to 5 (e.g., 0-3) groups chosen from —O—, —NH—, and —S—, substituted with a group $C(S)N(R)_2$, wherein R is hydrogen or substituted aryl (e.g., aryl substituted with a chelating moiety); and x is 1.

In other embodiments, each $R^1$ is hydrogen; $R^2$ is a substituted or unsubstituted $(C_1-C_{20})$hydrocarbyl group, interrupted by 0 to 5 (e.g., 0-3) groups chosen from —O—, —NH—, and —S—; Z is —NH—; and x is 1. In still other embodiments, each $R^1$ is hydrogen; Z is —NH—; x is 1; $R^2$ is a $(C_1-C_{20})$hydrocarbyl group, interrupted by 0 to 5 (e.g., 0-3) groups chosen from —O—, —NH—, and —S—, substituted with a group $C(S)N(R)_2$, wherein R is hydrogen or substituted aryl (e.g., aryl substituted with a chelating moiety). A non-limiting example of such an $R^2$ group is having the formula (III):

(III)

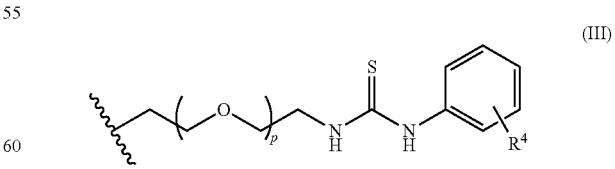

wherein p is an integer from 1 to 10 (e.g., 1 to 5 or 1 to 3); and $R^4$ is a chelating moiety (e.g., a 1,4,7,10-tetraazacyclododecane-1,4,7,10-tetraacetic acid (DOTA) radical). In some embodiments, the group having the formula (III) is a group of the formula (IIIa):

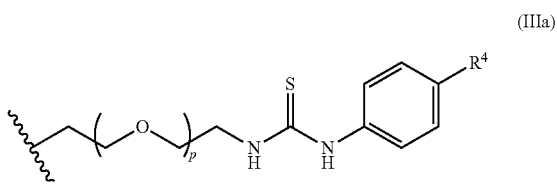

wherein p is an integer from 1 to 10 (e.g., 1 to 5 or 1 to 3); and $R^4$ is a chelating moiety (e.g., a DOTA radical).

In some embodiments, when the macrocyclic host molecule (A) comprises an $R^2$ group comprising a radical of a chelating moiety (e.g., a DOTA radical), the polyrotaxanes described herein are useful as MRI contrast agents, when the chelating moiety comprises a radionuclide, as the term is defined herein.

Polymer Chain (B)

The polymer chain (B), sometimes referred to as an "axle" herein, can be any suitable polymer chain, so long as the polymer chain can "thread" through a macrocylic host molecule or molecules and can interact with the polymer chain via host-guest hydrophobic interactions. For suitable polymer chains, see, e.g., C. J. Collins et al., *Biochemistry* 52: 3242-3253 (2013), which is incorporated by reference as if fully set forth herein. In some embodiments, suitable polymer chains "dethread" from the "axle" under certain conditions (e.g., under physiological conditions or in the presence of enzymes, when enzymes enzymatically remove the endcapping groups (C and C'), e.g., in NPC cells), such that the macrocyclic host molecule is released. The polymer chain (B) is a polymer chain of compatible dimensions. Suitable polymer chains (B) include, but are not limited to, those based on amine-terminated poly (tetrahydrofuran) and amine-terminated poly (ethylene glycol). See, e.g., Nakazono, K., et al., *Macromolecules* 43: 691-696 (2009), which is incorporated by reference as if fully set forth herein. Other suitable polymer chains (B) include polycarbonate and polyester polymers.

Suitable polymer chains (B) also include, but are not limited to, those based on polyalkylene oxide polymer chains that may be referred to herein, in some instances, as a "poloxamer core." Examples of polyalkylene oxide (e.g., random copolymer, di-block copolymer or tri-block copolyer arrangement) polymer chains (B) include those having the formula (IV):

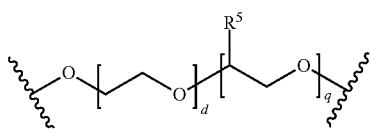

wherein each $R^5$ is independently a substituted or unsubstituted $(C_1$-$C_{20})$hydrocarbyl group (e.g., substituted or unsubstituted $(C_1$-$C_{12})$hydrocarbyl group; substituted or unsubstituted $(C_1$-$C_6)$hydrocarbyl group; or a substituted or unsubstituted $(C_1$-$C_3)$hydrocarbyl group); d is an integer from about 100 to about 800 (e.g., about 100 to about 500; about 250 to about 750; about 150 to about 400; about 250 to about 600 or about 300 to about 700); and q is an integer from about 100 to about 800 (e.g., about 100 to about 500; about 250 to about 750; about 150 to about 400; about 250 to about 600 or about 300 to about 700).

In some embodiments, each $R^5$ is independently a substituted or unsubstituted $(C_1$-$C_{20})$alkyl group (e.g., substituted or unsubstituted $(C_1$-$C_{12})$ alkyl group; substituted or unsubstituted $(C_1$-$C_6)$ alkyl group; or a substituted or unsubstituted $(C_1$-$C_3)$ alkyl group). In some embodiments, $R^5$ is methyl.

In some embodiments, d+q is from about 100 to about 800 (e.g., about 100 to about 500; about 250 to about 750; about 150 to about 400; about 250 to about 600 or about 300 to about 700). In other embodiments, d+q are such that the molecular weight of the polyalkylene oxide polymer chain (B) is from about 10 kD to about 50 kD (e.g., about 10 kD to about 35 kD, about 10 kD to about 20 kD, about 15 kD to about 25 kD or about 15 kD to about 30 kD).

Examples of polyalkylene oxide polymer chains (B) include polyalkylene oxide polymer chains based on poloxamers such as the PLURONIC® surfactants, a family of poly(ethylene glycol)-poly(propylene glycol)-poly(ethylene glycol) (PEG-PPG-PEG) triblock copolymers. PLURONIC® surfactants themselves, enjoy a wide range of applications due to their favorable biocompatibility and low toxicity. Examples of PLURONIC® surfactants include, but are not limited to PLURONIC® F127; PLURONIC® F68; PLURONIC® L35; PLURONIC® L64; and PLURONIC® L81.

Endcapping Groups (C and C')

The groups C and C' are the same or different and represent any suitable endcapping groups. For suitable endcapping groups, see, e.g., C. J. Collins et al., *Biochemistry* 52: 3242-3253 (2013), which is incorporated by reference as if fully set forth herein. The endcapping groups function generally to prevent the macrocyclic host molecule (A) or molecules from "dethreading" from the polymer chain (B) by, e.g., providing sufficient steric bulk. In some embodiments, the endcapping groups prevent the macrocyclic host molecule (A) or molecules from "dethreading" from the polymer chain (B) until an appropriate "trigger" is applied that removes the endcapping groups (e.g., under physiological conditions or in the presence of enzymes, when enzymes enzymatically remove the endcapping groups (C and C'), e.g., in NPC cells).

The groups C and C' are covalently attached to the polymer chain via a suitable linking group. Suitable endcapping groups include, but are not limited to, groups of the formula (IV):

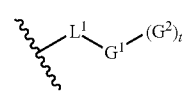

wherein $L^1$ is a $(C_1$-$C_6)$hydrocarbylene group; $G^1$ is a substituted or unsubstituted $(C_1$-$C_6)$hydrocarbylene group, interrupted by 0 to 5 (e.g., 0-3) groups chosen from —O—, —NH—, and —S—; $G^2$ is substituted or unsubstituted $(C_0$-$C_6)$hydrocarbylene-$(C_6$-$C_{50})$hydrocarbyl group (e.g., substituted or unsubstituted $(C_1$-$C_6)$hydrocarbylene-$(C_6$-$C_{50})$hydrocarbyl group), interrupted by 0 to 5 (e.g., 0-3) groups chosen from —O—, —NH—, and —S—, wherein the $(C_6$-$C_{50})$hydrocarbyl group is sterically bulky; and t is an integer from 2 to 5 (e.g., 2). In some embodiments, the $(C_6$-$C_{50})$hydrocarbyl group (e.g., $(C_6$-$C_{30})$hydrocarbyl; $(C_6$-$C_{20})$hydrocarbyl or $(C_6$-$C_{15})$hydrocarbyl) can be substituted or unsubstituted and can be, for example, a fluorescent moiety (e.g., fluorescein or a fluoresceinyl radical), a steroid (e.g., cholesterol or a cholesteryl radical) or an aryl group (e.g., a substituted aryl group).

In other embodiments, $L^1$ is a ($C_1$-$C_6$)hydrocarbylene group; $G^1$ is a substituted or unsubstituted ($C_1$-$C_6$)hydrocarbylene group, interrupted by 0 to 5 (e.g., 0-3) —NH— groups; $G^2$ is substituted or unsubstituted ($C_6$-$C_{50}$)hydrocarbylene-($C_1$-$C_6$)hydrocarbyl group, interrupted by 0 to 5 (e.g., 0-3) —NH— groups, wherein the ($C_6$-$C_{50}$)hydrocarbyl group is sterically bulky; and t is an integer from 2 to 5 (e.g., 2).

In some embodiments, $L^1$ is a ($C_1$-$C_3$)hydrocarbylene group; $G^1$ is a substituted or unsubstituted ($C_1$-$C_3$)hydrocarbylene group, interrupted by 0 to 5 (e.g., 0-3) groups chosen from —O—, —NH—, and —S—; $G^2$ is substituted or unsubstituted ($C_1$-$C_3$)hydrocarbylene-($C_6$-$C_{50}$)hydrocarbyl group, interrupted by 0 to 5 (e.g., 0-3) groups chosen from —O—, —NH—, and —S—, wherein the ($C_6$-$C_{50}$)hydrocarbyl group is sterically bulky; and t is an integer from 2 to 5 (e.g., 2).

In still other embodiments, $L^1$ is ($C_1$-$C_6$)acyl (e.g., C=O); $G^1$ is a substituted or unsubstituted ($C_1$-$C_3$)hydrocarbylene group, interrupted by 0 to 5 (e.g., 0-3) —NH— groups; $G^2$ is substituted or unsubstituted ($C_1$-$C_3$)hydrocarbylene-($C_6$-$C_{50}$)hydrocarbyl group, interrupted by 0 to 5 (e.g., 0-3) —NH— groups, wherein the ($C_6$-$C_{50}$)hydrocarbyl group is sterically bulky; and t is an integer from 2 to 5 (e.g., 2).

In some examples, $G^1$ and $G^2$, together, form a radical having the formula:

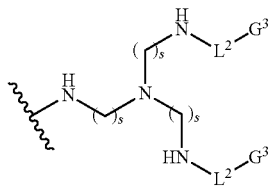

wherein each $L^2$ is independently a bond or ($C_1$-$C_6$)acyl (e.g., C=O); each $G^3$ is a substituted or unsubstituted ($C_6$-$C_{50}$)hydrocarbyl group, interrupted by 0 to 5 (e.g., 0-3) groups chosen from —O—, —NH—, and —S— (e.g., —O—), wherein the ($C_6$-$C_{50}$)hydrocarbyl group is sterically bulky; and each s is independently an integer from 1 to 6 (e.g., 2 to 5 or 2 to 3).

In some embodiments, the group $G^3$ is a substituted or unsubstituted —O—($C_6$-$C_{50}$)alkyl group or a substituted or unsubstituted ($C_6$-$C_{12}$)aryl group, wherein the ($C_6$-$C_{50}$)alkyl group and the ($C_6$-$C_{12}$)aryl group are sterically bulky. In other embodiments, the group $G^3$ is a substituted or unsubstituted —O—($C_6$-$C_{50}$)alkyl group, wherein, in some examples, the ($C_6$-$C_{50}$)alkyl group is a cholesteryl group:

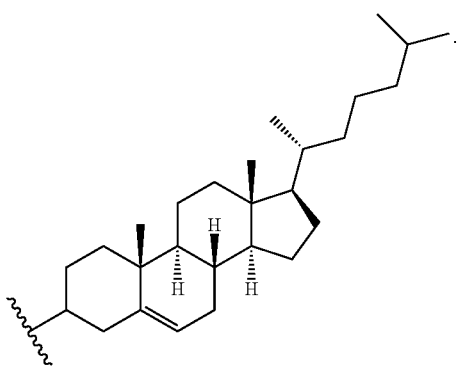

In other embodiments, $G^3$ is a substituted phenyl group, wherein the phenyl group is substituted with at least two substituents (e.g., $NO_2$). In some embodiments, the substituted phenyl group is a 2,4,6-trinitro phenyl group:

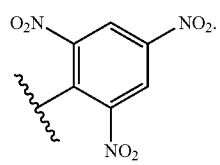

Polyrotaxanes

In some embodiments, the polyrotaxanes of the various embodiments of the present invention are compounds of the formula(V):

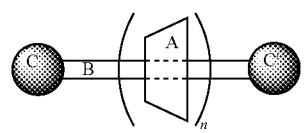

(V)

wherein:

C and C' are the same or different and comprise groups of the formula:

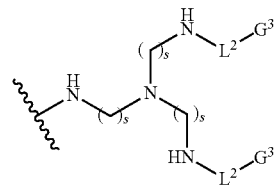

wherein each s is 2, each $L^2$ is a bond or C=O, and each $G^3$ is a cholesteryl group or a 2,4,6-trinitro phenyl group;

B represents a "polymer chain of compatible dimensions" of the formula:

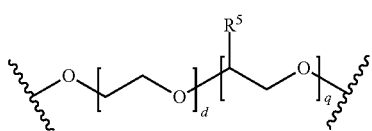

wherein R⁵ is methyl and d and q are as defined herein, to which the endcapping groups are covalently attached to the polymer chain via any suitable linking group (e.g., L¹ herein), including a suitable (C₁-C₆)hydrocarbylene group, such as a (C₁-C₆)acyl group; and A represents the macrocyclic host molecule of the general formula (I):

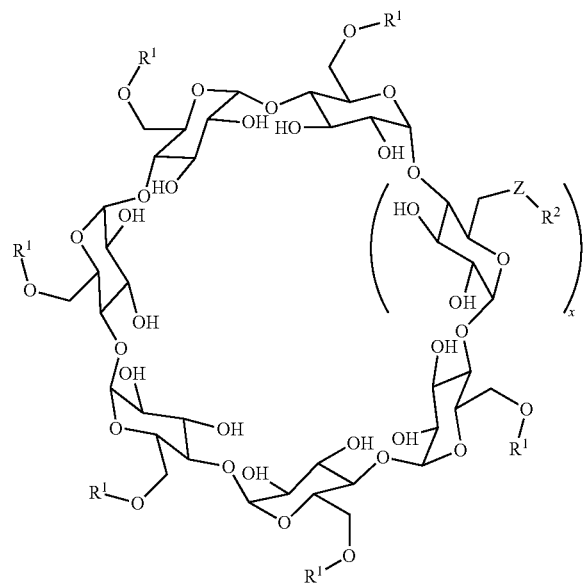

wherein R¹, R², Z, and x are as defined herein, wherein the macrocyclic host molecule is "threaded" onto the polymer chain B; and n is an integer from 1 to (e.g., 1 to 20, 1 to 15, 1 to 12, 2 to 12 or 2 to 18), wherein n represents the number of "copies" of the macrocyclic host molecules C that are "threaded" onto the polymer chain B. See, e.g., C. J. Collins et al., *Biochemistry* 52: 3242-3253 (2013), which is incorporated by reference as if fully set forth herein.

Those of ordinary skill in the art will recognize that compounds described herein (e.g., the macrocyclic host molecule (A)) contain chiral centers. All diastereomers of the compounds described herein are contemplated herein, as well as racemates.

Methods of Use
Niemann-Pick Type C Therapeutics

The polyrotaxanes of the various embodiments of the present invention are useful for treating Niemann-Pick type C (NPC) disease. NPC is a lysosomal storage disorder disease caused by accumulation of unesterified cholesterol and sphingolipids in the lysosomes of brain, liver, spleen, and lung cells. Aberrant accumulation of cholesterol in NPC cells has been shown to originate from mutation of the genes encoding either the membrane-bound NPC1 or the soluble NPC2 proteins required for cholesterol efflux from the lysosome. Unfortunately, the treatment options are limited for this typically fatal disease. Several studies have shown that β-cyclodextrin (β-CD) and its derivatives, including hydroxypropyl-β-cyclodextrin (HP-β-CD), are able to mobilize the removal of stored cholesterol from lysosomal compartments. Some groups have shown that the subcutaneous injection of HP-β-CD (4.0 mg/kg of body weight) into npc1⁻/⁻ mice produced an improvement in their survival, hepatopathology, and neuropathology. Although these results are promising, it is still unclear how HP-β-CD solubilizes cholesterol from cells in human NPC1 disease. Furthermore, high dosages of the administered HP-β-CDs are required since their persistence in the bloodstream is brief (>90% is cleared within 24 h) due to their appreciable water solubility and relatively low molecular weight (≈1460 g·mol⁻¹).

The polyrotaxanes of the various embodiments of the present invention can be long circulating; biocompatible; and can substantially increase cholesterol clearance from cells, such as NPC cells. Further, upon removal of the endcapping groups, they can deliver multiple "copies" of, e.g., HP-β-CD to the lysosomes of NPC cells. Analysis of certain polyrotaxanes of the various embodiments of the present invention in NPC2−/− fibroblast cells using filipin staining revealed that they promote the removal of aberrantly accumulated cholesterol from these cells. See Examples herein.

In some embodiments, therefore, the present invention contemplates methods for treating NPC comprising administering a therapeutically effective amount of at least one polyrotaxane of the various embodiments of the present invention or a composition (e.g., a pharmaceutical composition) comprising at least one polyrotaxane of the various embodiments of the present invention to a subject in need thereof.

In other embodiments, the present invention contemplates methods of removing cholesterol from the cells of an animal comprising administering a therapeutically effective amount of at least one polyrotaxane of the various embodiments of the present invention or a composition (e.g., a pharmaceutical composition) comprising at least one polyrotaxane of the various embodiments of the present invention to a subject in need thereof.

In some embodiments, the polyrotaxane contemplated for use in the methods for treating NPC or removing cholesterol from cells of an animal include, but are not limited to, polyrotaxanes having the general formula:

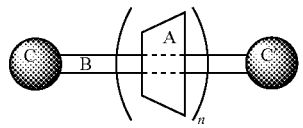

or a salt thereof,
wherein:
n is an integer from 1 to 30; C and C' are the same or different and represent endcapping groups of the formula:

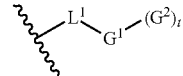

wherein L¹ is a (C₁-C₆)hydrocarbylene group, G¹ is a substituted or unsubstituted (C₁-C₆)hydrocarbylene group, interrupted by 0 to 5 groups chosen from —O—, —NH—, and —S—, G² is substituted or unsubstituted (C₁-C₆)hydrocarbylene-$(C_6-C_{50})$hydrocarbyl group, interrupted by 0 to 5 groups chosen from —O—, —NH—, and —S—, wherein the $(C_6-C_{50})$hydrocarbyl group is sterically bulky, and t is an integer from 2 to 5; B represents a polymer chain of the formula:

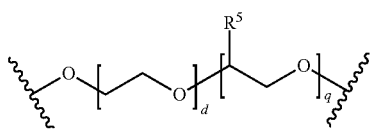

wherein each $R^5$ is independently a substituted or unsubstituted $(C_1-C_{20})$hydrocarbyl group, d is an integer from about 100 to about 800, and q is an integer from about 100 to about 800, wherein the polymer chain and the endcapping groups are covalently attached via any suitable linking group, including a suitable $(C_1-C_{20})$hydrocarbyl group (e.g., substituted or unsubstituted $(C_1-C_{12})$hydrocarbyl group; substituted or unsubstituted $(C_1-C_6)$hydrocarbyl group; or a substituted or unsubstituted $(C_1-C_3)$hydrocarbyl group), such as a $(C_1-C_6)$acyl group; and
A represents the macrocyclic host molecule of the general formula:

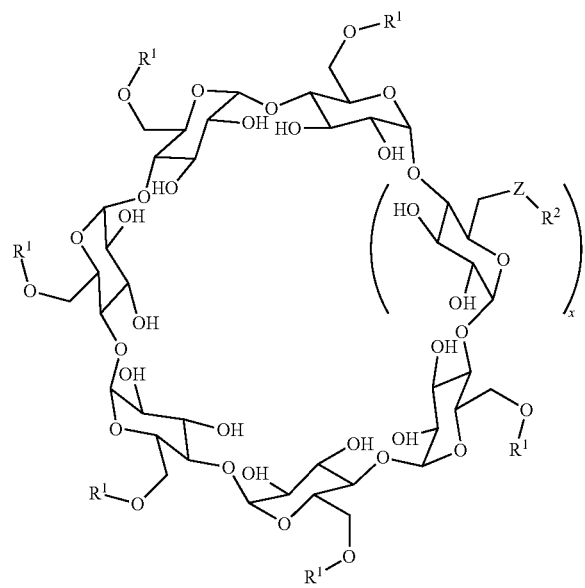

wherein each Z is O, each $R^1$ is independently hydrogen or a substituted or unsubstituted $(C_1-C_{20})$hydrocarbyl group, interrupted by 0 to 5 groups chosen from —O—, —NH—, and —S—; x is an integer from 1 to 3; and $R^2$ is substituted or unsubstituted $(C_1-C_{20})$hydrocarbyl group, interrupted by 0 to 5 groups chosen from —O—, —NH—, and —S—; with the proviso that at least one $R^1$ is a substituted or unsubstituted $(C_1-C_{20})$hydrocarbyl group, interrupted by 0 to 5 groups chosen from —O—, —NH—, and —S—.

Imaging Agents

Magnetic Resonance Imaging (MRI) is a powerful tool for high-resolution three-dimensional (3D) medical imaging of anatomical structures and specific organs or tissues within the body. MRI has advantages such as an absence of ionizing radiation, high contrast, high spatial resolution and excellent depth profiling capabilities. MRI has extensive applications in the diagnosis of various neurological, cardiovascular and oncological diseases. The quality and contrast of MRI images can be improved by the use of MRI contrast agents that enhance the image contrast within the tissue of interest by altering the longitudinal ($T_1$) and transverse ($T_2$) relaxation rates of the surrounding water protons. Contrast agents can be classified into either $T_1$ agents such as gadolinium (III) chelates, which increase the $T_1$ relaxation rate and produce a positive image contrast, or $T_2$ agents, such as supermagnetic iron oxide nanoparticles, which increase the $T_2$ relaxation rate and produce a negative image contrast.

A majority of clinically used contrast agents are $Gd^{3+}$ chelates, which are favored due to their high paramagnetism, excellent relaxation enhancement, and stability. Unfortunately, most clinically approved contrast agents suffer from rapid clearance from the body and ineffective contrast enhancement hence making them ineffective for angiographic enhancement. Thus, the use of nanoparticles as carriers for contrast agents are attractive due to their long circulating properties and potential for tissue selectivity through the use of targeting ligands. Not only do such nanoparticles have better pharmacokinetics, they potentially can also carry a much higher $Gd^{3+}$ loading. Nanoparticle platforms, such as dendrimers, polymers, liposomes, inorganic particles, and supramolecular assemblies, have been used as carriers of $Gd^{3+}$; however, most of these carriers suffer from issues such as acute toxicity and poor water accessibility due to $Gd^{3+}$ localization within the particle core. Additionally, most of the particles based on soft materials are restricted to a spherical shape due to the nature of their synthesis and/or assembly.

In some embodiments, the present invention contemplates a polyrotaxane comprising a poloxamer core and at least one cyclodextrin comprising at least one radionuclide chelating moiety. The polyrotaxanes of the various embodiments of the present invention can function as multivalent $Gd^{3+}$ carriers. For example, when the macrocyclic host molecule (A) comprises an $R^2$ group comprising a chelating moiety (e.g., a DOTA radical), the polyrotaxanes described herein are useful as imaging agents for MRI, when the chelating moiety comprises a radionuclide, as the term is defined herein.

In some embodiments, therefore, the present invention contemplates methods for imaging comprising administering an amount sufficient for imaging of a polyrotaxane according to the various embodiments of the present invention or a composition comprising an amount sufficient for imaging of a polyrotaxane according to the various embodiments of the present invention, to a subject in need thereof.

In some embodiments, the polyrotaxanes useful in the method for imaging include, but are not limited to, polyrotaxanes having the general formula

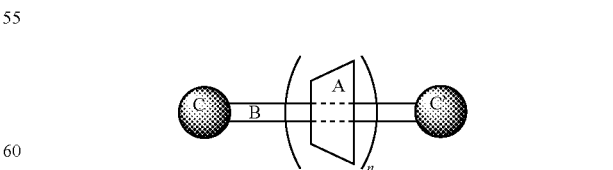

or a salt thereof,
wherein:
n is an integer from 1 to 30;
C and C' are the same or different and represent endcapping groups of the formula:

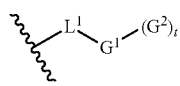

wherein $L^1$ is a $(C_1-C_6)$hydrocarbylene group, $G^1$ is a substituted or unsubstituted $(C_1-C_6)$hydrocarbylene group, interrupted by 0 to 5 groups chosen from —O—, —NH—, and —S—, $G^2$ is substituted or unsubstituted $(C_1-C_6)$hydrocarbylene-$(C_6-C_{50})$hydrocarbyl group, interrupted by 0 to 5 groups chosen from —O—, —NH—, and —S—, wherein the $(C_6-C_{50})$hydrocarbyl group is sterically bulky, and t is an integer from 2 to 5;

B represents a polymer chain of the formula:

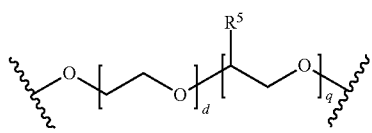

wherein each $R^5$ is independently a substituted or unsubstituted $(C_1-C_{20})$hydrocarbyl group, d is an integer from about 100 to about 800, and q is an integer from about 100 to about 800, wherein the polymer chain and the endcapping groups are covalently attached via any suitable linking group, including a suitable $(C_1-C_{20})$hydrocarbyl group (e.g., substituted or unsubstituted $(C_1-C_{12})$hydrocarbyl group; substituted or unsubstituted $(C_1-C_6)$hydrocarbyl group; or a substituted or unsubstituted $(C_1-C_3)$hydrocarbyl group), such as a $(C_1-C_6)$acyl group; and A represents the macrocyclic host molecule of the general formula:

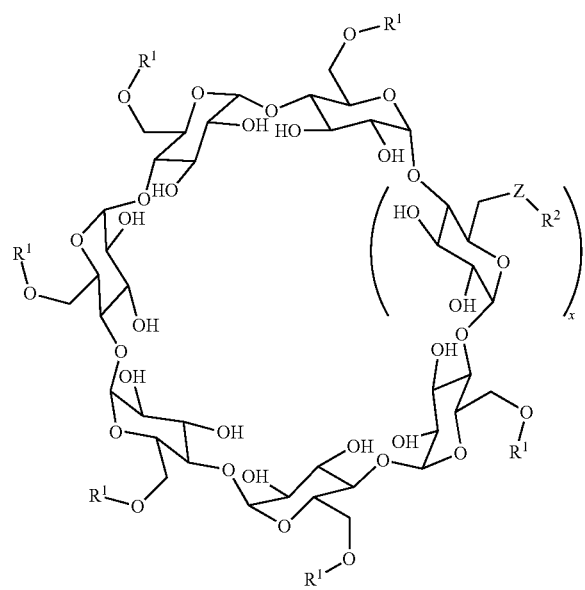

wherein each Z is independently O or NH, each $R^1$ is independently hydrogen or a substituted or unsubstituted $(C_1-C_{20})$hydrocarbyl group, interrupted by 0 to 5 groups chosen from —O—, —NH—, and —S—; x is an integer from 1 to 3; and $R^2$ is substituted or unsubstituted $(C_1-C_{20})$ hydrocarbyl group, interrupted by 0 to 5 groups chosen from —O—, —NH—, and —S—; with the proviso that at least one $R^2$ is $(C_1-C_{20})$hydrocarbyl group, interrupted by 0 to 5 groups chosen from —O—, —NH—, and —S—, substituted with a group $C(S)N(R)_2$, wherein one R is hydrogen and the other is an aryl group substituted with a radionuclide chelating moiety.

Methods of Making Polyrotaxanes

Embodiments of the present invention contemplate methods of making the rotaxanes of the various embodiments of the present invention by combining/contacting a suitable polymer chain (B) with a suitable macrocyclic host molecule (A) (e.g., under heterogeneous conditions) under non-aqueous conditions (e.g., in the presence of a non-polar solvent, such as diethyl ether, hexane or the like). In some embodiments, a suitable polymer chain (B) and a suitable macrocyclic host molecule (A) are contacted for an amount of time sufficient (e.g., 48 hours) for the macrocyclic host molecule (A) to "thread" onto the polymer chain (B), such that at least one (e.g., 1 to 30, 1 to 20, 1 to 15, 5 to 15, 3 to 11, 1 to 12, 2 to 12 or 2 to 18) macrocyclic host molecule is threaded onto the polymer chain. The ends of the polymer chain (B), comprising that at least one (e.g., 1 to 30, 1 to 20, 1 to 15, 5 to 15, 3 to 11, 1 to 12, 2 to 12 or 2 to 18) macrocyclic host molecule threaded onto the polymer chain are subsequently "capped" using the capping methods described herein or those known in the art. See, e.g., C. J. Collins et al., *Biochemistry* 52: 3242-3253 (2013), which is incorporated by reference as if fully set forth herein.

Pharmaceutical Compositions

Various embodiments of the present invention also contemplate pharmaceutical compositions comprising one or more compounds of the various embodiments of the present invention and one or more pharmaceutically acceptable excipients. A "pharmaceutical composition" refers to a chemical or biological composition suitable for administration to a subject (e.g., an animal, such as, but not limited to, a mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multilayer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal, oral, and intravenous. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Local administration can also be administration to the cell, tissue, organ, and/or organ system, which requires imaging (e.g., magnetic resonance imaging).

Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

The term "therapeutically effective amount" as used herein, refers to that amount of one or more compounds of the various embodiments of the present invention that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

Definitions

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof.

As used herein, the term "hydrocarbylene" broadly refers to a divalent functional group derived from a straight chain, branched, or cyclic hydrocarbon, such as an alkylene (e.g., —$CH_2$— and —$CH_2CH_2$—), alkenylene (e.g., —CH═CH— and —CH═CH—$CH_3$, wherein, when applicable, the double bond geometry may be E-, Z- or a mixture of E- and Z-), alkynylene (e.g., —C≡C— and —C≡C≡CH$_3$), arylene (e.g., phenylene), cycloalkylene (e.g., cylcopentylene and cyclohexylene), divalent acyl (e.g., —C(=O)— and —CH$_2$C(=O)—CH$_2$), or a combination thereof. Hydrocarbylene groups can be unsubstituted or substituted, as defined herein.

The hydrocarbyl group can be substituted or unsubstituted. The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. The "substituent" can also be an organic group. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups.

The term "organic group" as used herein refers to but is not limited to, any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be hydrogen (in examples that include other carbon atoms) or a carbon-based moiety (e.g., alkyl, cycloalkyl, heterocycloalkyl, aryl, and heteroaryl), and wherein the carbon-based moiety can itself be further substituted.

Organic groups also include chelating moieties, also referred to herein as "nuclide chelating moiety," such as, but not limited to, diethylenetriamine pentaacetic acid (DTPA), 1,4,7,10-tetraazacyclododecane-1,4,7,10-tetraacetic acid (DOTA), triethylenetetramine (TETA), 1,4,7-triazacyclononane-triacetic acid (NOTA), and the like, that are capable of chelating, e.g., a radionuclide or a paramagnetic nuclide. Examples of radionuclides include, but are not limited to, In-111, Y-90, F-18, P-32, Sc-47, Cu-62, Cu-64, Cu-67, Ga-67, Ga-68, Y-86, Y-90, Zr-89, Tc-99m, Pd-109, Ag-111, In-111, I-123, I-125, I-131, Sm-153, Gd-155, Gd-157, Th-161, Lu-177, Re-186, Re-188, Pt-197, Pb-212, Bi-212, Bi-213, Ra-223, Ac-225, As-72, As-77, At-211, Au-198, Au-199, Bi-212, Br-75, Br-76B, C-11, Co-55Co, Dy-166, Er-169, F-18, Fe-52, Fe-59, Ga-67, Ga-68, Gd-154-158, Ho-166, I-120, I-121, I-124, In-10, In-111, M194, Lu-177, Mn-51, Mn-52, Mo-99, N-13, O-15, P-32, P-33, Pb-211, Pb-212, Pd-109, Pm-149, Pr-142, Pr-143, Rb-82, Re-189, Rh-105, Sc-47, Se-75, Sr-83, Sr-89, Th-161, Tc-94, Tc-99, Y-86, Y-90 and Zr-89. Examples of paramagnetic nuclides include, but are not limited to Gd$^{3+}$, Mn$^{2+}$, and Fe$^{3+}$.

Non-limiting examples of substituents, J, that can be bonded to a substituted carbon (or other) atom include F, Cl, Br, I, OR, OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R)$_2$, SR, SOR, SO$_2$R', SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted with J; or wherein two R groups bonded to a nitrogen atom or to adjacent nitrogen atoms can together with the nitrogen atom or atoms form a heterocyclyl, which can be mono- or independently multi-substituted with J.

The term "alkyl" and "alkylene," as used herein, refer to substituted or unsubstituted straight chain and branched alkyl and alkylene groups and cycloalkyl and cycloalkylene groups having from 1 to 50 carbon atoms, 10 to 30 carbon atoms, 12 to 18 carbon atoms, 1 to about 20 carbon atoms, 1 to 10 carbons, 1 to 8 carbon atoms 1 to 5 carbon atoms or, in some embodiments, from 1 to 3 carbon atoms. Examples of straight chain alkyl groups include those with from 1 to 8 carbon atoms such as methyl, ethyl, n-propyl, n-butyl, n-pentyl, n-hexyl, n-heptyl, n-octyl groups. Examples of branched alkyl groups include, but are not limited to, isopropyl, iso-butyl, sec-butyl, t-butyl, neopentyl, isopentyl, 2,2-dimethylpropyl, and isostearyl groups. As used herein, the term "alkyl" and "alkyelen" encompasses n-alkyl and n-alkylene; isoalkyl and isoalkylene; and anteisoalkyl and anteisoalkylene groups as well as other branched chain forms of alkyl and alkylene.

The term "alkenyl" and "alkenylene," as used herein, refer to substituted or unsubstituted straight and branched chain and cyclic alkyl and alkylene groups as defined herein, except that at least one double bond exists between two carbon atoms. Thus, alkenyl and alkenylene groups have from 2 to 50 carbon atoms, or 2 to about 20 carbon atoms, or 2 to 12 carbons or, in some embodiments, from 2 to 8 carbon atoms. Examples of alkenyl groups include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" and "alkynylene," as used herein, refer to substituted or unsubstituted straight and branched chain alkyl and alkylene groups, except that at least one triple bond exists between two carbon atoms. Thus, alkynyl and alkynylene groups have from 2 to 50 carbon atoms, 2 to about carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-50 additional carbon atoms bonded to the carbonyl group. An acyl group can include double or triple bonds within the meaning herein. An acryloyl group is an example of an acyl group. An acyl group can also include heteroatoms (e.g., —O—, —NH—, and —S—). A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" and "arylene," as used herein, refer to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl and arylene groups contain about 6 to about 14 carbons in the ring portions of the groups. Representative substituted aryl groups can be mono-substituted or substituted more than once, such as, but not limited to, 2-, 3-, 4-, 5-, or 6-substituted phenyl or 2-8 substituted naphthyl groups.

The term "heterocyclyl," as used herein, refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 40 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —$CF(CH_3)_2$ and the like.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

EXAMPLES

The present invention can be better understood by reference to the following examples which are offered by way of illustration. The present invention is not limited to the examples given herein.

Materials.

PLURONIC® triblock copolymers F127 (EO 200, PO 65), F68 (EO 153, PO 29), L35 (EO 22, PO 16,), L64 (EO 26, PO 30), and L81 (EO 6, PO 43) were purchased from Sigma Aldrich and dried by azeotropic distillation from benzene under vacuum before use. 2-Hydroxypropyl-β-cyclodextrin, carbonyldiimidazole (CDI), triethylamine (TEA), tris(2-aminoethyl)amine (TAEA), were also purchased from Sigma-Aldrich and were used directly. 2,4,6-Trinitrobenzenesulfonic acid (TNBS) solution, 10% w/v in water, was obtained from Research Organics in Cleveland, Ohio and used as received. All solvents were distilled from an appropriate desiccant prior to use. Dialysis cellulose membranes were obtained from Spectrum Labs Inc. and immersed in deionized water for at least 30 min prior to use. Ultra-pure water (resistivity≈18.0 MΩ/cm$^{-1}$) was generated from a NANOpure Ultrapure water system.

Ultraviolet-Visible Spectroscopy.

Absorption spectra, recorded using a HP8453 UV-Vis spectrophotometer equipped with tungsten and deuterium lamps, were measured to confirm the effectiveness of, e.g., TNBS endcapping reactions of polyrotaxanes of the various embodiments of the present invention. The samples were dissolved in water (1 mg/mL) and spectra were recorded at 20° C.

Matrix Assisted Laser Desorption Ionization Time-of-Flight, MALDI-TOF.

MALDI-MS spectra were acquired over a mass range of 1500-35000 Da in positive-ion reflector mode on an Applied Biosystems/MDS Sciex 4800 MALDI-TOF/TOF Analyzer with 4000 Series Explorer v3.5 software using a laser power of 6000 and 6500 laser shots in linear mode. The matrix included a freshly prepared ionic liquid matrix (ILM) made using a previously described protocol with some modifications. Briefly, 2',4',6'-trihydroxyacetophenone monohydrate (THAP) and 1,1,3,3-tetramethylguanidine (TMG) were mixed at a molar ratio of 1:2 in methanol. The solution was then sonicated for 15 min at 40° C. After removal of methanol by centrifugal evaporation in a SpeedVac for 3 h at 20° C., ILMs were left under a 50 µm Hg vacuum overnight. Final ILM solutions were then prepared at a concentration of 90 mg/mL in DMF for use as a matrix. The polyrotaxanes samples were prepared at 3 mg/mL in DMF and then mixed in a 1:80 polyrotaxane:ILM ratio for MALDI-MS analysis. Then, 0.6 µL of a polyrotaxane:ILM mixture was deposited onto a mirror-polished stainless steel MALDI target and allowed to dry at 20° C. under atmospheric pressure overnight before analysis.

Atomic Force Microscopy.

Topology (size, height) of polyrotaxane particles were determined in air at 22° C. by tapping-mode atomic force microscopy using a Multimode AFM equipped with Nanoscope IIIa controller (Veeco Instruments, USA), an uncoated probe tip of 10 nm of less (NSC15/A1BS, MikroMasch, USA), and cantilevers having a spring constant of 40 N/m. In a typical measurement, 7.0 µL of a polyrotaxane sample (1.0×10$^{-9}$ mg/mL in water) were deposited onto a mica surface after cleaning by probe sonication and water removal using a TechSpray duster containing 1,1,1,2-tetrafluoroethane gas.

High-Performance and Ultra-Performance Liquid Chromatography, HPLC/UPLC.

An Agilent Series 1200 HPLC coupled with an ESA Corona detector was employed for the dethreading studies of polyrotaxanes of the various embodiments of the present invention. In this assay, the cyclodextrin peak in the chromatogram was integrated and the concentration of HP-β-CD, obtained from the polyrotaxanes cleavage, was determined by comparison with a standard curve for 1 mL aliquots of aqueous solution of polyrotaxane solution that were treated with one of two different buffers (pH 7.4 and pH 5.5) at 37° C. The aqueous solutions of polyrotaxanes (2.0 mg/mL) were filtered through a 0.2 µm cellulose membrane filter before injection. The calibration curve was constructed by analyzing different concentrations of HP-β-CD standard dissolved in water. The separation was performed at 50° C. on an Agilent reversed-phase Zorbax Eclipse XDB-phenyl column (2.1 mm×150 mm, particle size 5 µm). The mobile phase composition was a mixture of water (A) and acetonitrile (B) in the gradient elution at a flow-rate of 0.25 mL/min. The water/acetonitrile mixture composition was as follows: 0-9 min, water (100%), 9-11 min, water/acetonitrile (40/60, v/v), 11-12 min, water/acetonitrile (29/71, v/v), and 12-25 min, water (100%). UPLC-MS analysis was performed as an independent measurement to determine the percentage of free cyclodextrin in the samples using a Thermo Accela UPLC system (Thermo Fisher Scientific, Waltham, Mass., USA) coupled to a Thermo LTQ Velos mass spectrometer. A lab-made hydrophilic interaction column (2.1×30 mm, 700 nm nonporous silica particles coated with polyacrylamide) was used as the stationary phase. The temperature of the column oven was maintained at 25° C. Stock solutions of HP-β-CD were prepared at different concentrations in the range of 0.05-2 mg/mL in water as calibration standards.

Cell Culture Rescue Study of Polyrotaxanes.

To assess the therapeutic potential of, among other polyrotaxanes of the various embodiments of the present invention, HP-β-CD:PLURONIC® polyrotaxanes in an appropriate tissue culture model, human NPC2 deficient fibroblast cells (npc2$^{-/-}$) were grown and treated with the polyrotaxanes. Each compound was solubilized in DMSO and diluted in fibroblast cell culture media (MEM/15% FBS/pen/strep) to a concentration yielding the equivalent of 25 µM free HP-β-CD and a final DMSO concentration of 0.001%. The old medium was removed from cells and the media containing each polyrotaxane sample was added before fixing the cells at 30 min, 1.0 h, 3.0 h, and 6.0 h post-treatment. The fixed cells were then stained with 0.05 mg·ml$^{-1}$ Filipin followed by slide preparation. The reduction of cholesterol accumulation was monitored qualitatively by imaging the filipin stain in the cells, and quantitatively by the determination of filipin stain area to total cell area. Results are expressed relative to control untreated cells and are represented as mean±SE (n=3).

Example 1

The synthesis of HP-β-CD:poloxamer polyrotaxanes was performed via the sequence shown in Scheme 2, wherein d, q, n are as defined herein and A, B, C, and C' are as shown.

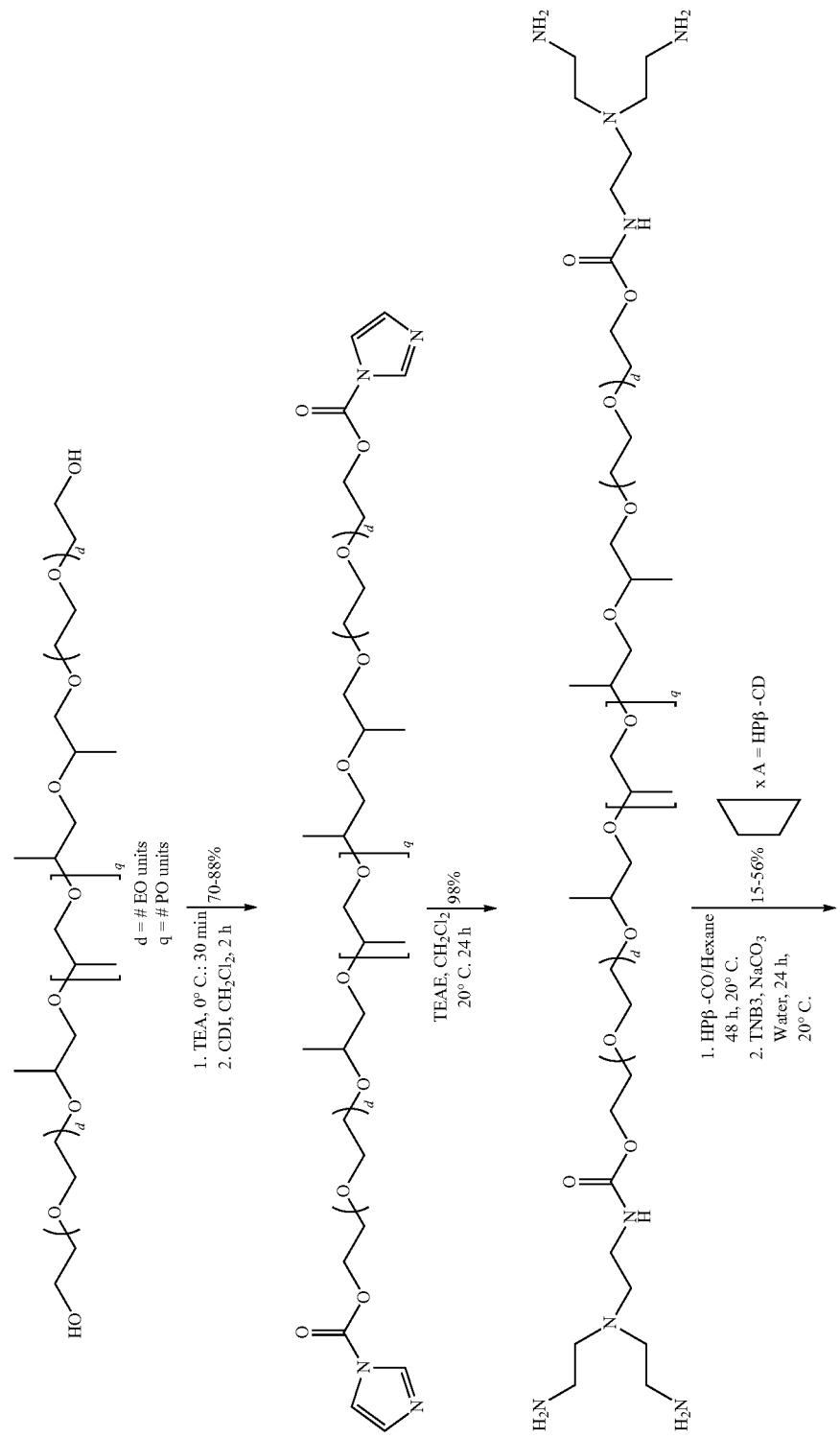

-continued
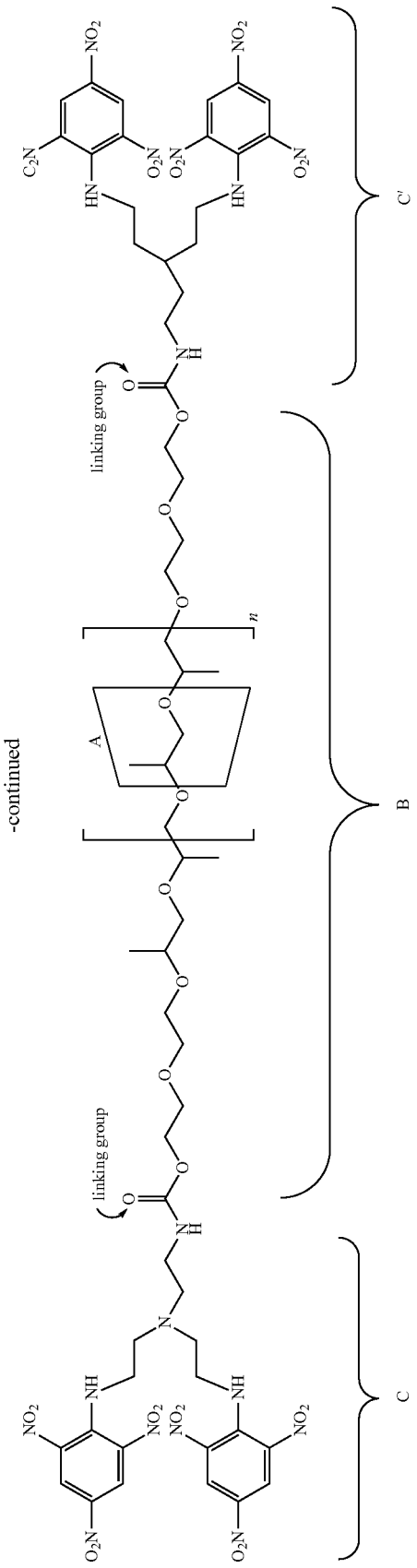

Preparation of α, ω-bis-tris(2-aminoethyl)amine PLURONIC® Triblock Copolymer (TAEA-PLURONIC®)

The typical synthetic procedure of the TAEA-PLURONIC® derivatives is described as follows. Dried PLURONIC® copolymer (0.400 mmol) was dissolved in 30 mL dry $CH_2Cl_2$. Triethylamine (1.5 equiv.) was slowly added over 30 min on an ice bath. The mixture was allowed to slowly warm up to 20° C. before addition of excess of CDI (20.0 mmol). This mixture was then stirred under nitrogen for 24 h at 20° C. and concentrated with a rotary evaporator. The product was precipitated in 500 ml ether and filtered in the cases of solid PLURONICs® (F127 and F68). The crude product was washed with ether, filtered, and vacuum dried to afford 70-98% of white powder of α, ω-bis-carbonylimidazole PLURONIC® triblock copolymer. In the case of liquid PLURONICs® (L35, L64, L81), the products were washed by centrifugation (8000 rpm, 5 min, 20° C.). The crude CDI-activated PLURONIC® intermediates (3.53 g; 0.276 mmol) were dissolved in 30 mL dry $CH_2Cl_2$ before addition of tris(2-aminoethyl)amine (13.8 mmol). The mixture was then stirred under dried $N_2$ at 20° C. for 24 h. The product was precipitated in 300 mL ether and washed three times with diethyl ether by either centrifugation (liquid PLURONICs®) or filtration (solid PLURONICs®). The final product was dried under a 50 m Hg vacuum for 72 h to yield either white powders or yellow liquids of α,ω-bis-tris(2-aminoethyl)amine PLURONIC® intermediates (PLURONIC®-TAEA). $^1$H NMR ($D_2O$): δ=1.00 ppm (m, $CH_3$ of PPG), 2.60-2.80 ppm (m, 16H, $CH_2$ of TAEA), 3.54-3.65 ppm (m, $CH_2$ of PEG, and PPG, CH of PPG).

Preparation of TNBS-Endcapped Polyrotaxanes. General Protocol.

Dried PLURONIC®-TAEAs (0.04 mmol) and 2-hydroxypropyl-β-cyclodextrin (i.e., ratio of CD:PPG unit=1:2) were dissolved (or suspended) in 15 mL hexane and the mixture vortexed for 3 min before vigorously stirring for 2 h. Then, bath sonication for 30 min at 30° C. followed by 5 min probe sonication (Model W-350, 50 w, ½" probe) were performed to improve the threading efficiency of the PLURONIC® copolymers. The mixture then was stirred for 48 h at 20° C. and shaken on a rocking plate for an additional 24 h before removal of hexane and addition of water to make a slurry solution to which 2,4,6-trinitrobenzenesulfonic acid solution (10% w/v in water, 0.24 mmol) and $NaHCO_3$, (0.24 mmol) were added. The mixture was stirred at 20° C. for 24 h and then mixed an additional 24 h on a rocking plate to allow the products to aggregate and precipitate. The unreacted reagents and unthreaded cyclodextrins were removed by twice dissolving the crude product in 10 mL of methanol and precipitating the product by addition of 500 ml diethyl ether. The product was purified by dialysis using 3,500-14,000 MWCO regenerated cellulose membranes in deionized water for 8 d and dried by lyophilization to generate yellow-orange powders of polyrotaxanes. $^1$H NMR (DMSO-$d_6$): δ=8.7 μm (s, 8H, meta H of phenyl), 5.0 ppm (b, $C_1$—H of CD), 4.0 ppm (t, 4H, phenyl C—NH) 3.5-3.8 ppm (m, $C_{3,5,6}$—H of CD), 2.6-2.8 ppm (m, 16H, $CH_2$ of TAEA) 1.0 ppm (d, $CH_3$ of PPG).

Example 2

The preparation of tris(2-aminothyl)amine-modified poloxamers was achieved by slight modification of the method reported by Li and coworkers. Li, J. et al., *Advanced Materials* 18: 2969-2974 (2006). Organic solvents were explored the use of organic solvents for the threading reaction. Several solvents (3 mL) were used to dissolve 100 mg of PLURONIC® F127-TAEA and HP-β-CD in a 2:1 PPG:CD ratio. The turbid solutions were sequentially bath and probe sonicated, followed by stirring at 20° C. for 48 h. Low boiling solvents (e.g., DCM, methanol, diethyl ether, ethyl acetate, and hexane) were removed under reduced pressure to yield white pseudopolyrotaxane intermediates. Subsequent addition of an excess 2,4,6-trinitrobenzene sulfonate (TNBS) slurry solution in the presence of $NaHCO_3$, followed by stirring of the orange viscous solutions at 20° C. for 24 h, produced endcapped polyrotaxanes that were purified by solvent washing and dialysis. For rotaxanation reactions in higher boiling solvents such as water, DMSO, and DMF, the TNBS endcapping reagent was added directly, followed by a washing and dialysis purification procedure. A summary of the impact of solvent type on the reaction yield of polyrotaxane and corresponding percent coverage of the PLURONIC® PPG block is shown below in Table 1.

TABLE 1

Solvent effect on yield of HP-β-CD: PLURONIC ® F127.

| Solvent | $\varepsilon^a$ | mg | No. of CD$^b$ | Coverage ratio (%)$^c$ |
| --- | --- | --- | --- | --- |
| water | 79 | 2.2 | 0 | 0 |
| $D_2O$ | 78 | 5.2 | 0 | 0 |
| DMSO | 46 | 14 | 0 | 0 |
| DMF | 37 | 39 | 0 | 0 |
| methanol | 33 | 1.4 | 0 | 0 |
| dichloromethane | 9.1 | 6.8 | 1 | 3 |
| Ethyl acetate | 6.0 | 24 | 4 | 12 |
| diethyl ether | 4.2 | 17 | 9 | 28 |
| hexane | 1.9 | 86 | 11 | 34 |

PLURONIC® F127 (Mn 12600, 100 mg), HP-β-CD (Mw 1460, 0.34 g, 1 CD/2 PO units), stirred in solvent (3 mL) for 48 h at 20° C. before addition of TNBS (0.046 mmol, 0.14 mL) and stirring at 20° C. for 24 h. a e: dielectric constant, b Number of HP-β-CD units threaded, c Determined by 1H NMR integration, based on the ratio of $C_1$—H protons of HP-β-CD and methyl protons of PPG (assuming 1 CD/2 PPG units).

$^1$H NMR spectroscopy analysis was used to determine the number of cyclodextrins "threaded" onto the PLURONIC® axle by comparing integral intensities of the HP-β-CD $C_1$—H (5.05 ppm) and PPG $CH_3$ (1.0 ppm) signals. The coverage ratio was calculated based on the assumption that two PPG units are included per CD unit. Our data show that non-polar solvents such as hexane and diethyl ether promote higher threading efficiencies than water, $D_2O$, methanol, DMSO, or DMF, which show little or no sign of HP-β-CD in the product NMR spectra. It can be inferred from these findings that polar solvents drive the polar cyclodextrins to aggregate through hydrogen bond interactions between the "wide" and "narrow" faces of the toroid, thereby forming hydrophobic tunnels that enable inclusion of the PLURONIC® chains. Additionally, while not being bound by any particular theory, non-polar solvents appear to prevent self-association of the PLURONIC® copolymers by solvating their lipophilic PPG blocks. The polyrotaxane structure, obtained by threading HP-β-CD onto PLURONIC® F127 in hexane solution, was confirmed by $^1$HNMR. A proton peak at ~1.0 ppm is assigned to the PPG methyl groups on the copolymer, whereas proton signals in the 3-3.5 ppm region are attributed to the methylene units (CH$_2$) of the PEG and some of the HP-β-CD protons. A broad signal displayed in the 4.5-5.0 ppm region is assigned to the HP-β-CD C$_1$—H proton as well as the OH-8 proton of the hydroxypropyl cyclodextrin modification. The aromatic TNB proton signals can be observed further downfield in the region of 7-8 ppm. The average number of HP-β-CD units that were threaded onto the PPG block was estimated from the relative intensities of the $^1$H NMR signals attributed to the C$_1$—H, OH-8 HP-β-CD peaks and the PPG/CH$_3$ doublet.

To further confirm the rotaxanation reaction between HP-β-CD and the F127 PLURONIC® axle, two-dimensional-NOESY $^1$H NMR spectra were collected. The inner C$_{3,5}$—H protons of HP-β-CD display a spatial correlation with the PPG methyl groups. This result is consistent with previous reports for β-CD-polymer complexes, suggesting that HP-β-CD molecules were threaded onto the F127 PLURONIC® chains. Furthermore, to prove that the end capping reaction was effective, UV-visible spectroscopy was performed on aqueous solutions (0.5 mg/mL) of HP-β-CD: F127 PLURONIC® polyrotaxane and free TNBS. The absorption maxima of the polyrotaxane complex (ca. 345 nm, 422 nm) differ completely from that of the unreacted TNBS precursor. This finding confirms that the corresponding HP-β-CD:F127 PLURONIC® pseudopolyrotaxane was fully endcapped.

The same reaction conditions in hexane were implemented to prepare polyrotaxanes based on other poloxamers (PLURONIC® copolymers F68, L35, L64, L81, with differing PEG and PPG block lengths). In these cases, 0.04 mmol was used for all the other poloxamers, dissolved in 15 mL of hexane for the threading reaction.

Table 2 summarizes the effect of PPG block size on the percent coverage relative to the maximum theoretical coverage possible for the PPG block. As it can be seen, the threading efficiency is inversely proportional to the hydrophilic-lipophilic balance (HLB) of the poloxamer axle, with high coverages observed for PLURONIC® L81 and PLURONIC® L64. These findings are consistent with our hypothesis that non-polar solvents favor the rotaxanation reaction by promoting interactions between the hydrophobic PPG block and the hydrophobic cavity of the self-associated HP-β-CD monomers. PLURONIC® F127 is an exception to this trend, likely due to the large PEG blocks that flank the PPG core, thereby suppressing the rotaxanation reaction due to weaker hydrophobic interactions between the cyclodextrin cavity and the PEG blocks.

of HP-β-CD molecules threaded onto the PLURONIC® core as determined by 1H NMR integration. The free CD values (w/v) were determined by UPLC chromatography using HP-β-CD as standard. The average size and height of the polyrotaxane products were determined from AFM images of the final products. HLB: Hydrophilic-Lipophilic Balance, CAC: critical aggregation concentration. a values adapted from P. Laibinis et al., *J. Coll. Interface. Sci.* 1991, 142, 74.

MALDI-TOF MS Analysis of HP-β-CD:Poloxamer Polyrotaxanes.

MALDI-TOF mass spectrometry was used to determine the distribution of molar masses of the polyrotaxane products formed by the sequence shown in Scheme 2.

NMR spectroscopy and SEC chromatography are the most common methods employed for polyrotaxane characterization, however, analysis of polydimethyl siloxane:cyclodextrin polyrotaxane compositions and molecular weights using MALDI-TOF can also be used. 1:80 polyrotaxane: ILM matrix composition, initially evaluated for HP-β-CD: PLURONIC® F127 polyrotaxane, with the THAP/TMG mixture (1:2 ratio in methanol) was found to produce the best signal-to-noise ratios. FIG. SI3 shows the spectra of all five polyrotaxanes. In each spectrum, a range of peaks corresponding to different degrees of HP-β-CD threading ($n_{CD}$) were observed. The peak intensity was found to decrease with increasing polyrotaxane m/z values, until the signal was no longer discernible from the base line. For all polyrotaxanes, the observed m/z values corresponded to the sum of TNB-endcapped poloxamer chains+1460× $n_{CD}$. Interestingly, the spectra reveal stepwise increment of mass differing by 1460 Da, corresponding to the molar mass of the HP-β-CD monomer. Furthermore, the most intense ion peak families were in agreement with the values calculated by NMR as summarized in Table 2, however, the spectral profiles show that the polyrotaxane products are polydisperse compounds (MALDI-TOF spectra can be seen in the supporting information).

AFM Imaging of Polyrotaxanes.

Using tapping-mode AFM, microstructures of aggregated polyrotaxaness were observed. All the polyrotaxanes appear as large globular aggregates of different sizes, with average diameters ranging between 47 to 80 nm and heights varying between 0.5-2 nm. These data show that the polyrotaxane molecules cluster into spherical assemblies, presumably due to lateral hydrogen bond interactions between the rotaxan-

TABLE 2

Molecular Weight and Purity of Polyrotaxanes

| Polyrotaxane | HLB$^a$ | CAC (%)$^a$ | % Free CD (UPLC) | $n_{CD}$ | Threading efficiency | Mw (NMR) | Mw (MALDI) | Average height (nm) | Average size (nm) |
|---|---|---|---|---|---|---|---|---|---|
| 07HP.F127 | 22 | 0.004 | 3.3 | 7 | 22 | 24008 | 24939 | 2.20 | 80 |
| 02HP.F68 | 29 | 0.04 | 0.90 | 2 | 15 | 12458 | 13059 | 1.30 | 50 |
| 04HP.L35 | 19 | 1 | 2.3 | 4 | 44 | 8928 | 8109 | 0.81 | 61 |
| 06HP.L64 | 15 | 0.14 | 6.0 | 6 | 43 | 12848 | 13248 | 1.30 | 70 |
| 11HP.L81 | 2 | 0.0063 | 1.5 | 11 | 52 | 20048 | 17611 | 0.39 | 48 |

In Table 2, and elsewhere herein, the notation nHP.XXX refers to the number n of HP-β-CD molecules that are "threaded" onto a poloxamer "axle," wherein XXX denotes the type of poloxamer "axle."

The threading efficiency was calculated based on a presumed 1 HP-β-CD:2 PO unit ratio. nCD refers to the number ated hydroxypropyl-β-cyclodextrins. The combination of low threading efficiencies and flexible, unthreaded PEG ends promotes the aggregation of the hydrophobic PPG-HP-β-CD domains into spherical particles that are surrounded by a PEG corona as reported by Zhang et al. The spherical appearance of these particles suggests that they may possess attractive long-circulation properties in vivo by avoiding their rapid clearance from blood via renal filtration.

Example 3

NPC2$^{-/-}$ Fibroblast Cell Response to Polyrotaxane Exposure.

The non-covalent association of HP-β-CD with poloxamer-based polyrotaxanes confers these polymers with the ability to readily dethread the cyclodextrin units from the polymer axles upon removal of the endcapping group due to, e.g., enzymatic activation. Several enzymatic activation schemes have been evaluated recently, however, none have been reported for NPC cells. To investigate polyrotaxanes that will release HP-β-CD upon activation within NPC cells to promote cholesterol solubilization and efflux from the lysosome, the endcap cleavage reaction and dethreading kinetics were investigated of HP-β-CD:poloxamer polyrotaxane complexes that were exposed to buffers of different as a mimic of their response to neutral (pH 7.4) and acidic endosome compartments (pH 5.5). HPLC analysis of F127 based-polyrotaxane (07HP.F127, 2 mg/mL) exposed to either PBS buffer, pH 7.4 or citrate buffer, pH 5.5 at 37° C. revealed that the HP-β-CD: PLURONIC® F127 polyrotaxane is stable toward both mildly acidic and neutral pH conditions. Although this result was encouraging in terms of the stability of the polyrotaxane particles under physiological conditions prior to endocytosis, it suggested that endcap cleavage from the polyrotaxane carrier within acidic late endosomes/lysosomes would be slow under these conditions. Suprisingly, however, treatment of npc2$^{-/-}$ fibroblasts, that have substantial pools of aberrantly stored cholesterol, with polyrotaxanes, produced a substantial and rapid decrease in filipin staining, providing a qualitative indication of cholesterol reduction within these cells. Time-dependent evaluation of filipin staining in these cells provided further evidence of reduced cholesterol accumulation for all the polyrotaxane compounds to levels that were similar to the extent of cholesterol reduction that is produced by 25 µM free HP-β-CD, i.e., 60 to 80% of untreated controls.

While not being bound by any particular theory, this finding suggests that the polyrotaxanes were internalized and dethreaded within the npc2$^{-/-}$ cells, thereby releasing free HP-β-CD that could then mobilize aberrantly stored cholesterol. Based on these findings, it is believed that the TNB group is cleaved from the polyrotaxane by either an enzymatic or reduction reaction occurring within the cells. There is a significant body of data indicating that nitrobenzene substrates are reduced by nitroreductase enzymes that are present in numerous human tissues. While not being bound any particular theory, based on these findings, and the sequential reduction mechanism of aromatic nitro compounds, it can be inferred that the carbamyl-linked trinitrobenzene endcaps of the polyrotaxanes are reduced to sterically smaller amine substituents that enable the cyclodextrins to slip off the polymer axles. An alternative explanation is that the carbamate linkage attaching the endcap to the polyrotaxane scaffold may serve as a substrate for tyrosinase hydrolysis, thus triggering endcap removal and subsequent dethreading of the polyrotaxane.

Example 4

A polyrotaxane-based Gd$^{3+}$ magnetic resonance (MR) imaging agent constructed from hydroxypropyl-β-cyclodextrin and a poloxamer (e.g., a triblock copolymer such as PEG-PPG-PEG) is described herein. A family of β-CD based polyrotaxanes possessing cleavable carbamate linkages to the polyrotaxane (PRTx) endcap were synthesized, having the formula:

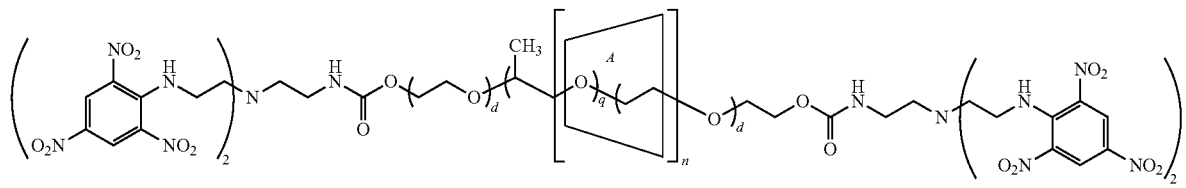

wherein d, q, n, and A are as defined herein.

These compounds have a poloxamer (e.g., a triblock copolymer such as PEG-PPG-PEG) core that has been threaded with either 5-15 copies of β-cyclodextrin (β-CD) (n=5-15) or 3-11 copies of 2-hydroxypropyl-β-cyclodextrin (HP-β-CD) (n=3-11) as shown in Tables 3 and 4:

TABLE 3

| Polymer Base (PLURONIC®) | n β-CD | % Threading | MW (NMR) | MW (GPC) | MW (AUC) |
|---|---|---|---|---|---|
| F127 | 15 | 71 | 30.8 kD | 33.3 kD | 30.0 |
| F68 | 14 | 100 | 25.5 kD | 28.5 kD | — |
| L64 | 12 | 92 | 11.0 kD | 13.1 kD | — |
| L35 | 5 | 62 | 17.7 kD | 17.1 kD | — |

TABLE 4

| Polymer Base (PLURONIC ®) | n HP-β-CD | % Threading | MW (NMR) |
|---|---|---|---|
| F127 | 11 | 34 | 29.8 kD |
| F68 | 4 | 29 | 15.3 kD |
| L64 | 4 | 27 | 7.5 kD |
| L35 | 3 | 36 | 10.0 kD |
| L81 | 5 | 23 | 11.3 kD |

Also synthesized were compounds of the formula:

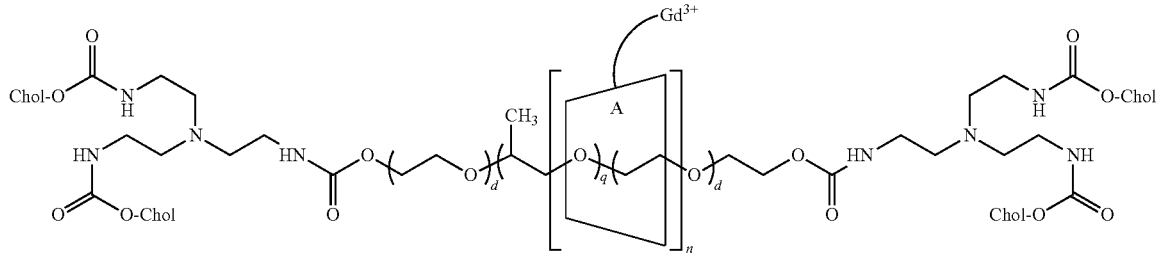

wherein Chol refers to a cholesteryl group; d, q, and n are as defined herein; and

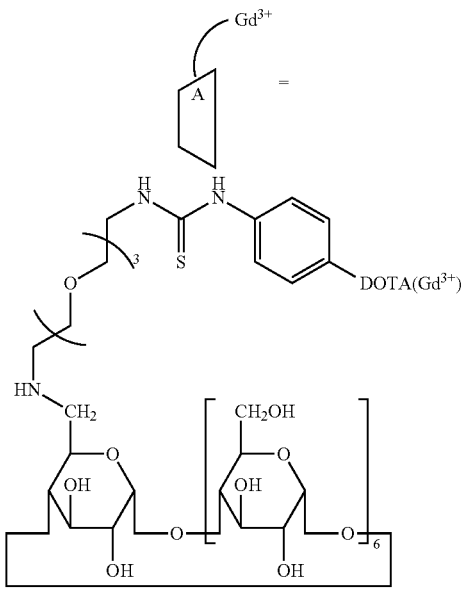

Such compounds are sometimes referred herein as "PRTx-DOTA" and "PRTx-DOTA(Rad)," when the compounds comprise one or more radionuclides (Rad) chelated by the DOTA.

Inclusion of the PPG blocks of the poloxamer by HP-β-CD was utilized to construct a polyrotaxane that retains the CD units via bis-carbamylcholesterol endcaps. While not being bound by any particular theory, the polyrotaxanes described herein appear to have a flexible rod-like morphology that can enhance their pharmacokinetics greatly by conferring them with long-circulating properties. Since HP-β-CD is known to form inclusion complexes with the PPG blocks of the poloxamer, this property was utilized to construct a polyrotaxane bearing cholesterol endcaps that were attached via carbamate linkages (HP-β-CD:F127-Chol).

Analysis by $^1$H NMR, 2D Nuclear Overhouser Effect Spectroscopy, and Matrix Assisted Laser Desorption/Ionization Mass Spectrometry (MALDI-MS) indicated that the polyrotaxane carried 15 copies of HP-β-CD, with a molecular weight of 35 kDa and PPG block coverage of ~46%. The polyrotaxane was also analyzed for presence of free HP-β-CD contamination by reverse phase high-pressure liquid chromatography and hydrophilic interaction liquid chromatography; both of these techniques indicated ≤10% free HP-β-CD. The HP-β-CD: F127-Chol was then modified with an excess of oligo(ethylene glycol) via CDI activated coupling to increase the water solubility of the material. Finally, this was conjugated to DOTA-Bn-NCS via a thiocarbamate linkage and then complexed with $Gd^{3+}$ to obtain the final PRTx-DOTA($Gd^{3+}$) with ~14 DOTA($Gd^{3+}$) moieties attached. The AFM images of the samples indicated that the polyrotaxane prepared had a rod-like morphology with lengths in the range of 30-40 nm AFM. Particles with dimensions between 3-7 nm are known to undergo rapid clearance from the bloodstream due to the effective pore size of the glomerular wall being around 8 nm. It was anticipated, therefore, that that the $Gd^{3+}$:DOTA-β-CD:poloxamer PRTx would have a much slower clearance rate from blood than the monomeric $Gd^{3+}$:DOTA-β-CD control due to flow alignment and enlargement of the effective PRTx rod diameter to ~4.6 nm due to the PEG-DOTA grafting.

The synthesized materials were then evaluated in a mouse model to determine their contrast enhancement capabilities. The MRI data reveals that PRTx-DOTA($Gd^{3+}$) had a 2-fold enhancement ratio (ER) in the heart for as long as 30 min. On the contrary, the ER of the control β-CD-DOTA($Gd^{3+}$) dropped from 1.5 to 1 over a period of 30 min. Furthermore, the MRI data also indicated that the ER observed in the kidney with the PRTx-DOTA($Gd^{3+}$) dropped from 2 to 1.6 over a period of 30 min, while that observed with the control β-CD-DOTA($Gd^{3+}$) dropped rapidly from 1.9 to 1.1 over a period of 30 min, hence indicating rapid renal filtration of the control. The superior MR contrast of the PRTx-DOTA ($Gd^{3+}$) in the heart at 30 min as compared to the control further confirmed the improved pharmacokinetics of the polyrotaxane. The increased molecular weight and dimensions of the β-CD constructs reduces their rate of kidney filtration due to the EPR effect after modification with $Gd^{3+}$:DOTA, leading to a substantially longer circulation half-life and enhancement ratios in mice for the polyrotaxane scaffold compared to the HP-β-CD monomer control. Furthermore, the polyrotaxanes were cleared through the bladder and no acute toxicity was observed. Exposure of Niemann-Pick Type C2−/− fibroblasts to the parent β-CD:poloxamer PRTx compound (i.e., prior to DOTA activation and $Gd^{3+}$ loading) reveals that the carbamyl-endcapped polyrotaxane structures remain intact in serum-supplemented media until they are trafficked to the LE/LY compartment, where the β-CD units are liberated from the polymer backbone via either pH- or enzyme-induced removal of the PRTx endcaps. While not being bound by any particular theory, these findings suggest that the PRTx may be excreted as an intact species. Further, these results taken together suggest that the PRTx-DOTA(Gd$^{3+}$) can be potential agents for vascular enhancement due to their lack of acute toxicity and long-circulating properties.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

The present invention provides for the following embodiments, the numbering of which is not to be construed as designating levels of importance:

Embodiment 1 relates to a polyrotaxane comprising a poloxamer core and at least one cyclodextrin comprising a nuclide chelating moiety.

Embodiment 2 relates to the polyrotaxane of Embodiment 1, wherein the nuclide chelating moiety is a radical of 1,4,7,10-tetraazacyclododecane-1,4,7,10-tetraacetic acid (DOTA).

Embodiment 3 relates to the polyrotaxane of Embodiments 1-2, further comprising at least one of a radionuclide and a paramagnetic nuclide chelated by the nuclide chelating moiety.

Embodiment 4 relates to the polyrotaxane of Embodiment 3, wherein the paramagnetic nuclide comprises Gd$^{3+}$.

Embodiment 5 relates to the polyrotaxane of Embodiments 1-4, wherein the polyrotaxane has the general formula:

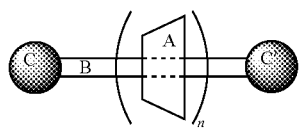

or a salt thereof,
wherein:
n is an integer from 1 to 30;
C and C' are the same or different and represent endcapping groups of the formula:

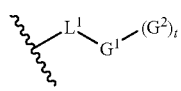

wherein
L$^1$ is a (C$_1$-C$_6$)hydrocarbylene group,
G$^1$ is a substituted or unsubstituted (C$_1$-C$_6$)hydrocarbylene group, interrupted by 0 to 5 groups chosen from —O—, —NH—, and —S—, G$^2$ is substituted or unsubstituted (C$_1$-C$_6$)hydrocarbylene-(C$_6$-C$_{50}$)hydrocarbyl group, interrupted by 0 to 5 groups chosen from —O—, —NH—, and —S—, wherein the (C$_6$-C$_{50}$) hydrocarbyl group is sterically bulky, and
t is an integer from 2 to 5;
B represents a polymer chain of the formula:

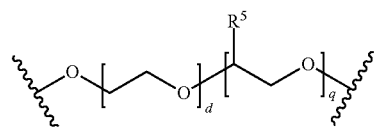

wherein
each R$^5$ is independently a substituted or unsubstituted (C$_1$-C$_{20}$)hydrocarbyl group,
d is an integer from about 100 to about 800, and q is an integer from about 100 to about 800; and
A represents the macrocyclic host molecule of the general formula:

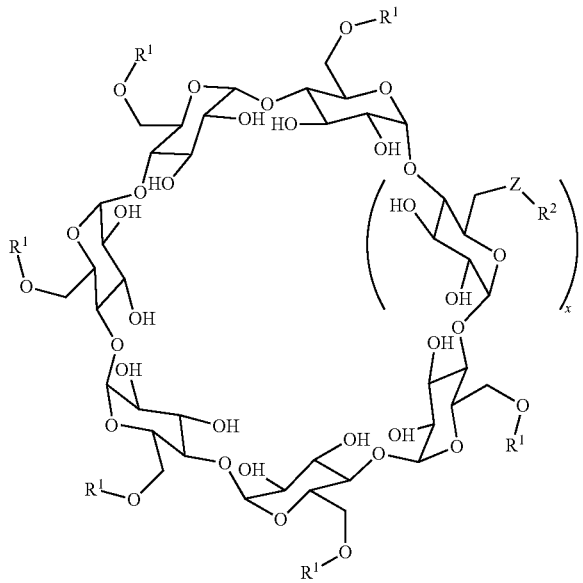

wherein
each Z is independently O or NH,
each R$^1$ is independently hydrogen or a substituted or unsubstituted (C$_1$-C$_{20}$)hydrocarbyl group, interrupted by 0 to 5 groups chosen from —O—, —NH—, and —S—;
x is an integer from 1 to 3; and
R$^2$ is substituted or unsubstituted (C$_1$-C$_{20}$)hydrocarbyl group, interrupted by 0 to 5 groups chosen from —O—, —NH—, and —S—;
with the proviso that at least one R$^2$ is (C$_1$-C$_{20}$)hydrocarbyl group, interrupted by 0 to 5 groups chosen from —O—, —NH—, and —S—, substituted with a group C(S)N(R)₂, wherein one R is hydrogen and the other is an aryl group substituted with a radionuclide chelating moiety.

Embodiment 6 relates to the polyrotaxane of Embodiment 5, wherein each $R^1$ is hydrogen.

Embodiment 7 relates to the polyrotaxane of Embodiments 5-6, wherein $R^2$ is:

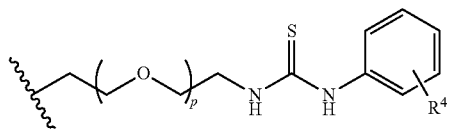

wherein p is an integer from 1 to 10; and $R^4$ is a radical of a chelating moiety.

Embodiment 8 relates to the polyrotaxane of Embodiments 5-7, wherein Z is —NH—; and x is 1.

Embodiment 9 relates to the polyrotaxane of Embodiments 5-8, wherein $L^1$ is $(C_1$-$C_6)$acyl.

Embodiment 10 relates to the polyrotaxane of Embodiments 5-9, wherein $G^1$ and $G^2$, together, form a radical having the formula:

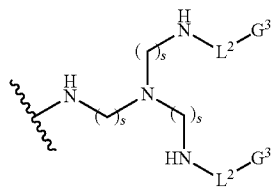

wherein each $L^2$ is independently a bond or acyl; each $G^3$ is a substituted or unsubstituted $(C_6$-$C_{50})$hydrocarbyl group, interrupted by 0 to 5 groups chosen from —O—, —NH—, and —S—, wherein the $(C_6$-$C_{50})$hydrocarbyl group is sterically bulky; and each s is independently an integer from 1 to 5.

Embodiment 11 relates to the polyrotaxane of Embodiment 10, wherein $G^3$ is a substituted or unsubstituted —O—$(C_6$-$C_{50})$alkyl group or a substituted or unsubstituted $(C_6$-$C_{12})$aryl group, wherein the $(C_6$-$C_{50})$alkyl group and the $(C_6$-$C_{12})$aryl group are sterically bulky.

Embodiment 12 relates to the polyrotaxane of Embodiments 10~11, wherein $G^3$ is a cholesteryl group or a 2,4,6-trinitro phenyl group.

Embodiment 13 relates to the polyrotaxane of Embodiments 5-12, wherein n is an integer from 5 to 15.

Embodiment 14 relates to the polyrotaxane of Embodiments 5-12, wherein n is an integer from 3 to 11.

Embodiment 15 relates to the polyrotaxane of Embodiment 5 having the structure:

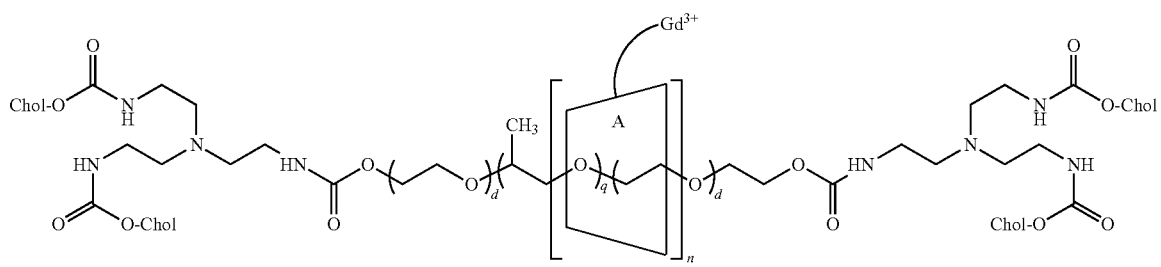

wherein:

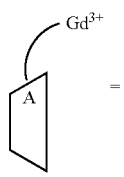

=

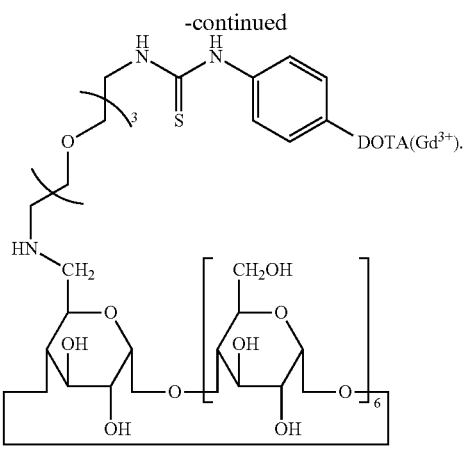

Embodiment 16 relates to a polyrotaxane having the general formula:

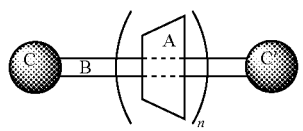

or a salt thereof,
wherein:
n is an integer from 1 to 30;
C and C' are the same or different and represent endcapping groups of the formula:

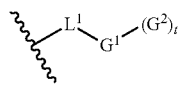

wherein
$L^1$ is a $(C_1\text{-}C_6)$hydrocarbylene group,
$G^1$ is a substituted or unsubstituted $(C_1\text{-}C_6)$hydrocarbylene group, interrupted by 0 to 5 groups chosen from —O—, —NH—, and —S—,
$G^2$ is substituted or unsubstituted $(C_1\text{-}C_6)$hydrocarbylene-$(C_6\text{-}C_{50})$hydrocarbyl group, interrupted by 0 to 5 groups chosen from —O—, —NH—, and —S—, wherein the $(C_6\text{-}C_{50})$hydrocarbyl group is sterically bulky, and
t is an integer from 2 to 5;
B represents a polymer chain of the formula:

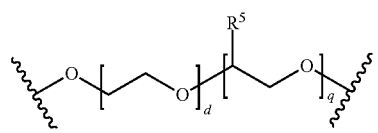

wherein
each $R^5$ is independently a substituted or unsubstituted $(C_1\text{-}C_{20})$hydrocarbyl group,
d is an integer from about 100 to about 800, and q is an integer from about 100 to about 800; and
A represents the macrocyclic host molecule of the general formula:

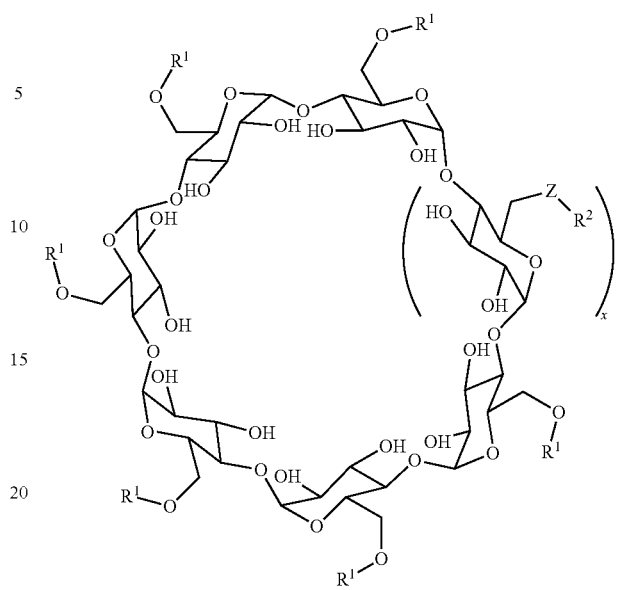

wherein
each Z is O,
each $R^1$ is independently hydrogen or a substituted or unsubstituted $(C_1\text{-}C_{20})$hydrocarbyl group, interrupted by 0 to 5 groups chosen from —O—, —NH—, and —S—;
x is an integer from 1 to 3; and
$R^2$ is substituted or unsubstituted $(C_1\text{-}C_{20})$hydrocarbyl group, interrupted by 0 to 5 groups chosen from —O—, —NH—, and —S—;
with the proviso that at least one $R^1$ is a substituted or unsubstituted $(C_1\text{-}C_{20})$hydrocarbyl group, interrupted by 0 to 5 groups chosen from —O—, —NH—, and —S—.

Embodiment 17 relates to the polyrotaxane of Embodiment 16, wherein at least one $R^1$ is a radical having the formula:

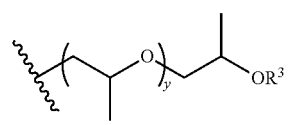

wherein y is an integer from 1 to 10.

Embodiment 18 relates to the polyrotaxane Embodiments 16-17 having the structure:

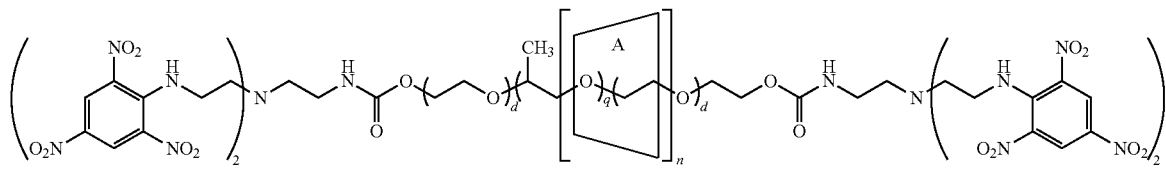

Embodiment 19 relates to a pharmaceutical composition comprising the polyrotaxane of Embodiments 1-18 and a pharmaceutically acceptable carrier.

Embodiment 20 relates to a method for treating Niemann-Pick type C (NPC) comprising administering a therapeutically effective amount of a polyrotaxane of Embodiments 16-19 or a composition comprising a polyrotaxane of Embodiments 16-19 to a subject in need thereof.

Embodiment 21 relates to a method for imaging comprising administering an amount sufficient for imaging of a polyrotaxane of Embodiments 3 or 5 or a composition comprising an amount sufficient for imaging of a polyrotaxane of Embodiments 3 or 5, to a subject in need thereof.

What is claimed is:

1. A polyrotaxane comprising the general formula:

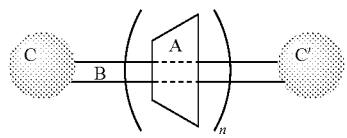

or a salt thereof,
wherein:
n is an integer from 1 to 30;
C and C' are the same or different and represent endcapping groups of the formula:

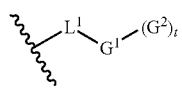

wherein:
$L^1$ is a ($C_1$-$C_6$)hydrocarbylene group,
$G^1$ and $G^2$, together, form a radical having the formula:

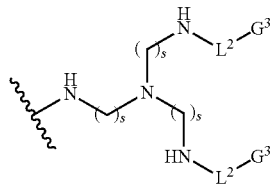

wherein each $L^2$ is independently a bond or acyl; each $G^3$ is a substituted or unsubstituted ($C_6$-$C_{50}$)hydrocarbyl group, interrupted by 0 to 5 groups chosen from —O—, —NH—, and —S—; and each s is independently an integer from 1 to 5; and t is an integer from 2 to 5:

B is a poly(ethylene glycol)-poly(propylene glycol)-poly(ethylene glycol) (PEG-PPG-PEG) triblock copolymer; and A is a beta cyclodextrin;

wherein $G^3$ is not a substituted or unsubstituted ($C_6$-$C_{12}$) aryl group.

2. The polyrotaxane of claim 1, wherein $G^3$ is a substituted or unsubstituted —O—($C_6$-$C_{50}$)alkyl group.

3. The polyrotaxane of claim 1, wherein $G^3$ is a cholesteryl group.

4. The polyrotaxane of claim 1, wherein n is an integer from 5 to 15.

5. The polyrotaxane of claim 1, wherein n is an integer from 3 to 11.

6. A pharmaceutical composition comprising the polyrotaxane of claim 1 and a pharmaceutically acceptable carrier.

7. The polyrotaxane of claim 1, wherein the poly(ethylene glycol)-poly(propylene glycol)-poly(ethylene glycol) (PEG-PPG-PEG) triblock copolymer has the formula:

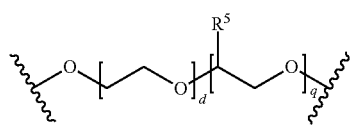

wherein each $R^5$ is methyl; d is an integer from about 100 to about 800; and q is an integer from about 100 to about 800.

8. The polyrotaxane of claim 7, wherein d+q is from about 100 to about 800.

* * * * *